(12) United States Patent
Dzau et al.

(10) Patent No.: US 10,130,637 B2
(45) Date of Patent: Nov. 20, 2018

(54) INHIBITION OF HISTONE METHYLTRANSFERASE FOR CARDIAC REPROGRAMMING

(71) Applicant: Duke University, Durham, NC (US)

(72) Inventors: Victor J. Dzau, Durham, NC (US); Maria Mirotsou, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 14/440,567

(22) PCT Filed: Nov. 4, 2013

(86) PCT No.: PCT/US2013/068352
§ 371 (c)(1),
(2) Date: May 4, 2015

(87) PCT Pub. No.: WO2014/071323
PCT Pub. Date: May 8, 2014

(65) Prior Publication Data
US 2015/0297611 A1    Oct. 22, 2015

Related U.S. Application Data

(60) Provisional application No. 61/721,800, filed on Nov. 2, 2012.

(51) Int. Cl.
| | | |
|---|---|---|
| *A61K 31/551* | (2006.01) | |
| *A61K 31/437* | (2006.01) | |
| *A61K 45/06* | (2006.01) | |
| *C07D 487/04* | (2006.01) | |
| *C07D 401/14* | (2006.01) | |
| *C12N 15/113* | (2010.01) | |
| *A61K 35/34* | (2015.01) | |

(52) U.S. Cl.
CPC .......... *A61K 31/551* (2013.01); *A61K 31/437* (2013.01); *A61K 35/34* (2013.01); *A61K 45/06* (2013.01); *C07D 401/14* (2013.01); *C07D 487/04* (2013.01); *C12N 15/1137* (2013.01); *C12Y 201/01043* (2013.01); *C12Y 201/01125* (2013.01); *C12Y 207/10002* (2013.01); *C12Y 207/11001* (2013.01); *C12N 2310/141* (2013.01); *C12N 2320/30* (2013.01)

(58) Field of Classification Search
None
See application file for complete search history.

(56) References Cited

U.S. PATENT DOCUMENTS

2009/0298910 A1   12/2009   Griffey et al.
2011/0110899 A1   5/2011    Shi et al.

FOREIGN PATENT DOCUMENTS

| WO | WO-2010033920 A2 | 3/2010 |
|---|---|---|
| WO | WO-2010090723 A2 | 8/2010 |
| WO | WO-2011133288 A1 | 10/2011 |
| WO | WO-2011139688 A2 | 11/2011 |
| WO | 2012006577 A2 | 1/2012 |
| WO | WO-2012067266 A1 | 5/2012 |
| WO | 2012108444 A1 | 8/2012 |
| WO | 2012133954 A1 | 10/2012 |
| WO | WO-2013033213 A1 | 3/2013 |
| WO | WO-2013063417 A1 | 5/2013 |

OTHER PUBLICATIONS

Chang et al. Nature Structural & Molecular Biology 16 (2009) 312-317.*
Shi et al. Cell Stem Cell 2008, 3, 568-574 published Nov. 6, 2008.*
Priori S. Circulation Research 2011, 109, 822-824.*
Ieda et al. Cell 2010, 142, 375-386.*
Haase et al. Cell Stem Cell 2009, 5, 434-441.*
Quattrocelli et al. Journal of Cellular Biochemistry 112:2006-2014 (2011).*
Huangfu et al., Induction of pluripotent stem cells by defined factors is greatly improved by small-molecule compounds. Nat Biotechnol. Jul. 2008;26(7):795-7.
Jayawardena et al., MicroRNA-mediated in vitro and in vivo direct reprogramming of cardiac fibroblasts to cardiomyocytes. Circ Res. May 2012; 25;110(11):1465-73.
Mezentseva et al., The histone methyltransferase inhibitor BIX01294 enhances the cardiac potential of bone marrow cells. Stem Cells Dev. Feb. 15, 2013;22(4):654-67.
Shi et al., A combined chemical and genetic approach for the generation of induced pluripotent stem cells. Cell Stem Cell. Jun. 5, 2008;2(6):525-8.
Thal et al., In vivo differentiation of epigenetically reprogrammed mouse and human endothelial progenitor cells into cardiomyocytes enhances functional and anatomical post-infarct myocardial repair. Circulation. 2011;124(21).
GenBank Accession No. NM_001256834.1.
GenBank Accession No. NM_001991.3.
GenBank Accession No. NM_004217.3.
GenBank Accession No. NM_004456.4.
GenBank Accession No. NM_019023.2.
GenBank Accession No. NM_020382.3.
GenBank Accession No. NM_030648.2.
GenBank Accession No. NM_031915.2.
GenBank Accession No. NP_001243763.1.
GenBank Accession No. NP_001982.2.
GenBank Accession No. NP_004208.2.

(Continued)

*Primary Examiner* — Jeffrey S Lundgren
*Assistant Examiner* — Michael J Schmitt
(74) *Attorney, Agent, or Firm* — Mintz Levin Cohn Ferris Glovsky and Popeo P.C.

(57) ABSTRACT

A method for promoting the reprogramming of a non-cardiomyocytic cell or tissue into cardiomyocytic cell or tissue comprising is carried out by contacting a non-cardiomyocytic cell or tissue with a modulator of histone methyltransferase activity or expression.

21 Claims, 13 Drawing Sheets

(56) References Cited

OTHER PUBLICATIONS

GenBank Accession No. NP_004447.2.
GenBank Accession No. NP_061896.1.
GenBank Accession No. NP_065115.3.
GenBank Accession No. NP_085151.1.
GenBank Accession No. NP_114121.2.
Takahashi et al., Induction of pluripotent stem cells from mouse embryonic and adult fibroblast cultures by defined factors. Cell. Aug. 25, 2006;126(4):663-76.
Takeuchi et al., Directed transdifferentiation of mouse mesoderm to heart tissue by defined factors. Nature. Jun. 4, 2009;459(7247):708-11.
Zhou et al., In vivo reprogramming of adult pancreatic exocrine cells to beta-cells. Nature. Oct. 2, 2008;455(7213):627-32.

* cited by examiner

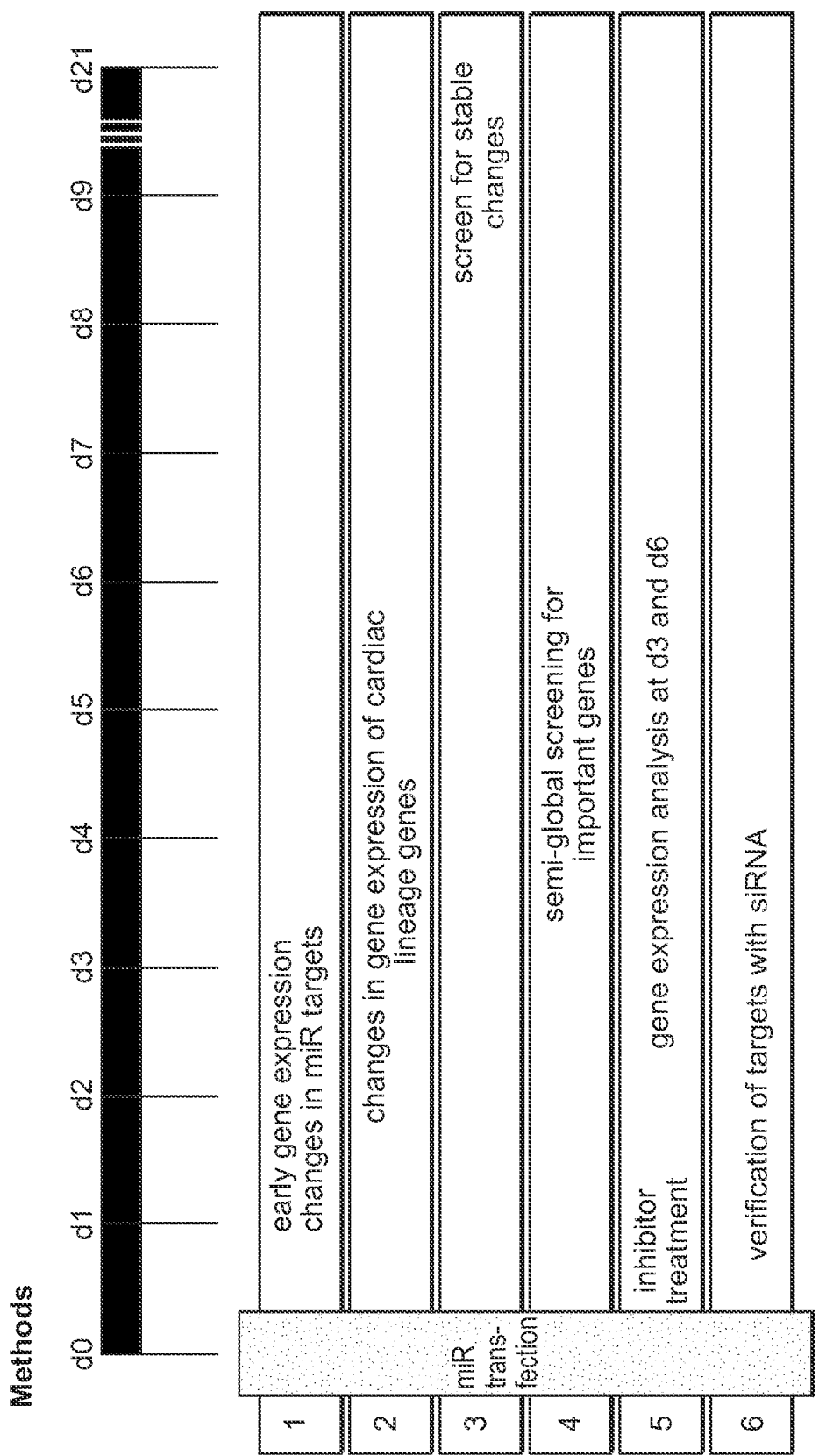

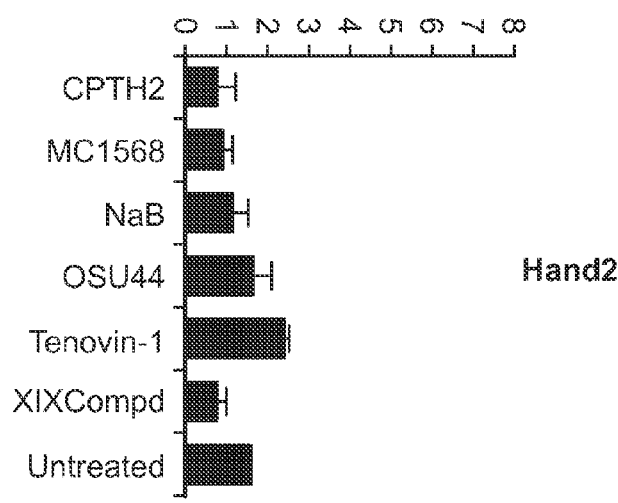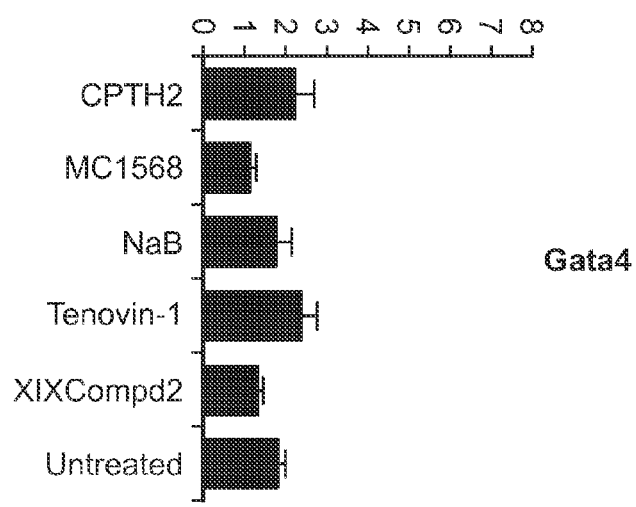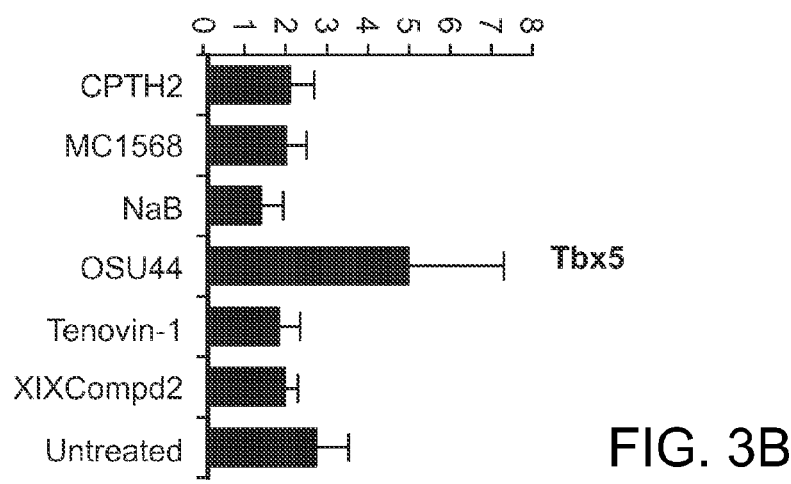
FIG. 3B

INHIBITION OF HISTONE METHYLTRANSFERASE FOR CARDIAC REPROGRAMMING

RELATED APPLICATIONS

This application claims priority to and benefit of U.S. Provisional Application No. 61/721,800, filed on Nov. 2, 2012; the contents of which are hereby incorporated in its entirety.

FIELD OF THE DISCLOSURE

This invention relates to the field of cardiology.

BACKGROUND OF THE DISCLOSURE

Cardiovascular disease and its manifestations, including coronary artery disease, myocardial infarction, congestive heart failure and cardiac hypertrophy, is the number one cause of death globally. In response to pathological stress, such as injury to the heart or myocardial infarction, cardiac fibroblasts and extracellular matrix proteins accumulate disproportionately and excessively to form scar tissue. This process is known as myocardial fibrosis. Because fibrotic scar tissue is not contractile and fails to contribute to cardiac function, myocardial fibrosis can result in mechanical stiffness, diminished cardiac function, contractile dysfunction, cardiac hypertrophy, and arrhythmias.

Heart tissue has a limited capacity for regeneration or self-renewal. Thus, repopulation of the injured or diseased heart with new, functional cardiomyocytes remains a daunting challenge. As such, there is a pressing need in the field of cardiology to develop new approaches for the regeneration of damaged or diseased cardiac tissue.

SUMMARY OF THE INVENTION

The present disclosure relates to a method for promoting conversion of cardiac fibrotic tissue into cardiomyocytic tissue is carried out by contacting non-cardiomyocytic cell or tissue into a cardiomyocoytic cell or tissue with a composition comprising a modulator of histone methyltransferase (HMT) activity or expression. The methods lead to direct reprogramming of differentiated cells such as fibroblasts to cardiomyocytes or cardiomyocyte progenitors. A method for promoting the direct reprogramming of fibrotic tissue (i.e., scar tissue) into cardiomyocytic cell or tissue by contacting the fibrotic tissue with a modulator of histone methyltransferase activity or expression. The modulator comprises a small molecule, a polynucleotide, or a polypeptide.

For example, the modulator comprises an inhibitor of histone methyltransferase expression or activity. An inhibitor of HMT activity is characterized as inhibition or reduction of methylation of proteins, preferably histones. For example, the modulator inhibits or reduces the expression or activity of Setdb2, Prmt7, Setd7, Setd8, Ezh1, Ezh2, or Aurkb. The inhibitors disclosed herein inhibit or reduce methylation lysine at position 9 on histone H3 (H3K9), lysine at position 27 on histone H3 (H3K27), or arginine at position 3 on histone H4 (H4R3). For example, the inhibition or reduction is 5%, 10%, 25%, 50%, 2-fold, 5-fold, 10-fold or less compared to the level of methylation or expression of the HMT before treatment. Preferably, the HMT inhibitors are BIX-01294 (trihydrochloride hydrate) (2-(Hexahydro-4-methyl-1H-1,4-diazepin-1-yl)-6,7-dimethoxy-N-[1-(phenylmethyl)-4-piperidinyl]-4-quinazolinamine trihydrochloride; Tocris Biosciences) or 3-Deazaneplanocin A hydrochloride (DZNep; Tocris Biosciences).

Alternatively, the modulator comprises an enhancer of histone methyltransferase expression or activity. An enhancer of HMT activity is characterized as enhancing or increasing methylation of proteins, preferably histones. For example, the modulator enhances or increases the expression or activity of Setdb2, Prmt7, Setd7, Setd8, Ezh1, Ezh2, or Aurkb. The inhibitors disclosed herein enhances or increases methylation lysine at position 9 on histone H3 (H3K9), lysine at position 27 on histone H3 (H3K27), or arginine at position 3 on histone H4 (H4R3). For example, the enhancement or increase is 1%, 2%, 5%, 10%, 25%, 50%, 2-fold, 5-fold, 10-fold or less compared to the level of methylation or expression of the HMT before treatment.

One example of a non-cardiomyocytic cell or tissue to be treated or reprogrammed as described herein is cardiac fibrotic tissue or scar tissue, e.g., scar tissue that has formed after heart tissue has been injured or diseased. Other examples include fibroblasts, adipocytes, or hematopoietic cells. The hematopoietic cells include CD34$^+$ umbilical cord blood cells. In preferred embodiments, non-cardiomyocytic cell is directly reprogrammed into a cardiomyocytic cell or cardiomyocytic progenitor cell without a stem cell intermediary state. The fibrotic tissue is present in a heart diagnosed as comprising myocardial infarction, ischemic heart disease, hypertrophic cardiomyopathy, valvular heart disease, congenital cardiomyopathy, or hypertension. The reprogramming methods are carried out by delivering the composition by local administration to the heart, preferably by intravenous administration or direct injection into cardiac tissue, for example at the site of the fibrotic tissue.

Administration is carried out using known methods of delivering therapeutic compounds to the heart, e.g., needle, catheter, or stent. In the case of combination therapy, compounds are administered together or sequentially. For example, a composition comprising the modulator of a histone methyltransferase is administered prior to, concurrently with, or after composition comprising another modulator of a histone methyltransferase, a JAK inhibitor, a histone deacetylase inhibitor, or a cardiovascular disease therapeutic agent.

The compositions and methods described herein offer an approach to treating cardiac disease long after the initial symptoms have occurred by directly converting, or reprogramming fibrotic tissue (i.e., fibroblasts) to cardiomyocytic cells or tissue, thereby directly replacing fibrotic tissue with viable functional cardiomyocytes. The fibrotic tissue is contacted with a composition comprising a modulator of histone methyltransferase expression or activity after fibrosis has developed as a result of myocardial infarction or other cardiac disease or injury process, e.g., days (1, 2, 3, 4, 5, 6 days after), weeks (1, 2, 4, 6, 8), months (2, 4, 6, 8, 10, 12), or even a year or more after the primary cardiac insult.
1. The present disclosure also provides methods for treating or reducing cardiac fibrosis by identifying a subject having or at risk of cardiac fibrosis and administering a modulator of histone methyltransferase activity or expression, in which the modulator causes reprogramming of cardiac fibrotic tissue into cardiomyocytic cells or tissue. In some aspects, the reprogramming is direct, without a stem cell intermediary state. Cardiac fibrosis can be determined or detected using methods recognized in the art, for example, histopathological staining for increased fibroblast markers or extracellular matrix proteins (e.g., collagen I, collagen II, collagen IV), detection of excessive proliferation of fibroblasts. Other signs that indicate for cardiac fibrosis include decreased exercise capacity, decreased cardiac ejection volume, decreased cardiac output, decreased cardiac index, increased collagen deposition, increased heart wall tension, increased pulmonary pressure, decreased diastolic pressure. Thus, the treating or reducing of cardiac fibrosis includes the method wherein said treating or reducing cardiac fibrosis comprises at least one selected from increasing exercise capacity, increasing cardiac ejection volume, decreasing left ventricular end diastolic pressure, decreasing pulmonary capillary wedge pressure, increasing cardiac output, increasing cardiac index, lowering pulmonary artery pressures, decreasing left ventricular end systolic and diastolic dimensions, decreasing collagen deposition in cardiac muscle or tissue, decreasing left and right ventricular wall stress, decreasing heart wall tension, increasing quality of life, decreasing disease related morbidity or mortality, or combinations thereof. These indications are measured by a clinician or physician using known methods in the clinical setting. As described herein, decreasing is 5%, 10%, 25%, 50%, 2-fold, 5-fold, 10-fold or less compared to before treatment. As described herein, increasing is 5%, 10%, 25%, 50%, 2-fold, 5-fold, 10-fold or more compared to before treatment.

An alternative method of restoring tissue specific function to fibrotic tissue in an organ is therefore carried out by providing patient-derived non-cardiomyocytic cells and contacting said non-cardiomyocytic cells with a histone methyltransferase inhibitor. Preferably, the non-cardiomyocytic cell is a fibroblast obtained from the subject to be treated. For example, the fibroblast is a cardiac fibroblast, an epidermal keratinocyte, or, preferably, a dermal fibroblast obtained from the skin of the patient to be treated. Cells can be cultured in vitro or ex vivo for 1 day, 1 week, 2 weeks, 3 weeks until the cells have a particular function, phenotype, or cell number. Cells can also be cultured under the appropriate conditions to enhance reprogramming efficiency, for example using particular growth medias (i.e., cardiomyocyte differentiation media) or treatment with additional agents known in the art to improve reprogramming efficiency, as disclosed herein). The cells are then harvested and, optionally, purified, before transplanting or injecting into the subject, preferably at the site for repair or regeneration. Cells directly reprogrammed in this manner are useful for cell replacement therapy, in which the reprogrammed cells are infused or injected into the cardiac tissue, for example, by intravenous injection or direct injection into the cardiac fibrotic tissue.

The invention therefore includes a purified population of primary fibroblasts treated with a histone methyltransferase modulator, as well as a purified population of cardiomyocytes or cardiomyocyte progenitors that were produced using the primary fibroblasts treated with a histone methyltransferase modulator. Each population is substantially free of stem cells, e.g., the population is at least 85%, 90%, 95%, 99%, or 100% transfected fibroblasts or at least 85%, 90%, 95%, 99%, or 100% reprogrammed myoblasts, cardiomyocytes, or cardiomyocyte progenitors. Cells are purified by virtue of selection based on cell surface markers as well as other cell selection techniques well known in the art.

As was discussed above, the cells are useful for therapeutic applications such as direct administration to a subject or as a component of another therapeutic intervention or device. For example, the invention encompasses a stent or catheter comprising the reprogrammed functional cardiomyocytic cells.

The composition and methods of the invention include several advantages over previous methods of reprogramming cells. For example, unlike methods that employ reprogramming to a stem cell phenotype and subsequent differentiation of this cell population, the direct reprogramming methods of the invention do not involve an intermediate stage of a stem cell phenotype. In addition, additional advantages of the use of small oligonucleotides, polypeptides, and small molecules rather than gene provides include ease of the production and development for biologic therapy.

The compositions are administered as pharmaceutically acceptable compositions, e.g., formulated with a pharmaceutically acceptable carrier or excipient. In general, dosage is from 0.01 µg to 100 g per kg of body weight, from 0.1 µg to 10 g per kg of body weight, from 1.0 µg to 1 g per kg of body weight, from 10.0 µg to 100 µg per kg of body weight, from 100 µg to 10 µg per kg of body weight, or from 1 µg to 5 µg per kg of body weight, and may be given once or more daily, weekly, monthly or yearly. Examples of dosages based on small animal studies are in the range of 80 µg/kg for single or multiple dosages. However, it is expected with appropriate modification dosages 1-25 µg/kg for single to three repeated dosages will confer clinical benefit in human subjects.

Optionally, the modulator of histone methyltransferase is administered in combination with another compound such as a small molecule or recombinant protein to increase reprogramming efficiencies. Such molecules suitable for increasing the efficiency of conversion to cardiac myocytes include bone morphogenetic protein 4 (BMP4), cardiomyocyte transcription factors, Janus protein tyrosine kinase (JAK)-1 inhibitor, and histone deacetylase inhibitors (HDIs). Examples of JAK1 inhibitors include, but are not limited to 2-(1,1-Dimethylethyl)-9-fluoro-3,6-dihydro-7H-benz[h]-imidaz[4,5-f]isoquinolin-7-one (CAS 457081-03-7; Millipore; EMD4 Biosciences) (also known as Pyridone 6); tofacitinib (CAS 540737-29-9; XELJANZ®, Pfizer; Sigma Aldrich); tyrphostin AG 490 (CAS 133550-30-8; Sigma Aldrich); cucurbitacin B hydrate (CAS 6199-67-3; Sigma Aldrich); baricitinib (LY3009104 or INCB028050) (CAS 1187594-09-7; Selleck Chemicals). Other reprogramming efficiency agents include RG108 (CAS 48208-26-0; Tocris Biosciences), R(+)Bay K 8644 (CAS 71145-03-4; Tocris Biosciences), PS48 (CAS 1180676-32-7; Tocris Biosciences), and A83-01 (Stemgent) (CAS 909910-43-6; Tocris Biosciences). Examples of histone deacetylase inhibitors (HDIs) include, but are not limited to valproic acid (CAS 1069-66-5; Tocris Biosciences), apicidin (CAS 183506-66-3; Sigma-Aldrich), M344 (amide analog of trichostatin) (CAS 251456-60-7; Sigma-Aldrich), sodium 4-phenylbutyrate (CAS 1716-12-7; Tocris Biosciences), splitomycin (CAS 5690-03-9; Sigma-Aldrich), trichostatin A (CAS 58880-19-6; Sigma Aldrich; Tocris Biosciences), SAHA (CAS 149647-78-9; Sigma-Aldrich; Cayman Chemical), SBHA (CAS 38937-66-5; Sigma Aldrich), Tubacin (CAS 537049-40-4; Enzo Life Sciences; Sigma-Aldrich), CI-994 (CAS 112522-64-2; Cayman Chemical; Tocris Biosciences), panobinostate (LBH589) (CAS 404950-80-7; BioVision Incorporated; LC Laboratories), APHA compound (CAS 676599-90-9; Sigma-Aldrich; Santa Cruz Biotechnologies), and BATCP (CAS 787549-23-9; Santa Cruz Biotechnologies; Sigma-Aldrich). Examples of cardiomyocyte transcription factors include, but are not limited to, GATA-4 and Mef2.

Pharmaceutical compositions are also provided herein, comprising a modulator of a histone methyltransferase and a pharmaceutically acceptable excipient. The modulator comprises an inhibitor or enhancer of histone methyltransferase expression or activity. The modulator inhibits or reduces, or enhances or increases the expression or activity of Setdb2, Prmt7, Setd7, Setd8, Ezh1, Ezh2, or Aurkb. The modulator inhibits or reduces, or enhances or increases methylation of lysine at position 9 on histone H3 (H3K9), lysine at position 27 on histone H3 (H3K27), or arginine at position 3 on histone H4 (H4R3). For example, the HMT inhibitors are BIX-01294 (trihydrochloride hydrate) or 3-Deazaneplanocin A hydrochloride (DZNep). The pharmaceutical compositions comprised herein are suitable for administration for local administration to the cardiac tissue, for example, by intravenous injection or direct injections to the site of injury, damage, or fibrosis.

The subject is preferably a mammal in need of such treatment, e.g., a subject that has been diagnosed with cardiac fibrosis (e.g., scar tissue; excessive deposition of collagen or other extracellular matrix proteins; or excessive proliferation of cardiac fibroblasts) or a predisposition thereto. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

All compounds, polynucleotides, polypeptides, and small molecules of the invention are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds, e.g., small molecules, are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant a compound that has been separated from the components that naturally accompany it. For example, the nucleotides and polypeptides are substantially pure when they are at least 60%, 70%, 80%, 90%, 95%, or even 99%, by weight, free from the proteins and naturally-occurring organic molecules with they are naturally associated and compounds such as small molecules are purified from starting reagents, intermediates, or other synthesis components. The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1 is a diagram showing an overview of experimental design and methods. Fibroblast transfections were performed using known methods, e.g., as described in Jayarwadena et al., 2012, Circ. Res. Microarray data analysis was performed using standard tools such as with Toppgene (www.toppgene.cchmc.org), STRING (http://string-db.org), as well as GeneGo Metacore (www.genego.com/metacore.php). Each of the references are hereby incorporated by reference.

FIGS. 3A and 3B are bar graphs showing that HDACs are not affecting early stages of miR mediated cardiac reprogramming. The graphs display gene expression fold changes normalized to NegmiR transfection. Data are shown as mean±SEM. *P<0.05. FIG. 3A shows HDAC gene expression profile at 4 d post transfection, and FIG. 3B shows the results of treatment with several different inhibitors against modifiers of histone acetylation (CPTH2 inhibitors all HAT activity, MC1568 affects HDAC class II, NaB mainly affects HDAC class I, OSU44 inhibits class I, II and IV, Tenovin-1 inhibits all class III Hdacs and XIX Compd2 selectively inhibits HDAC8). All inhibitors were administered 24 hours post treatment. Gene expression of cardiac transcription factors was measured 6 d post transfection.

DETAILED DESCRIPTION

Figure 2A:
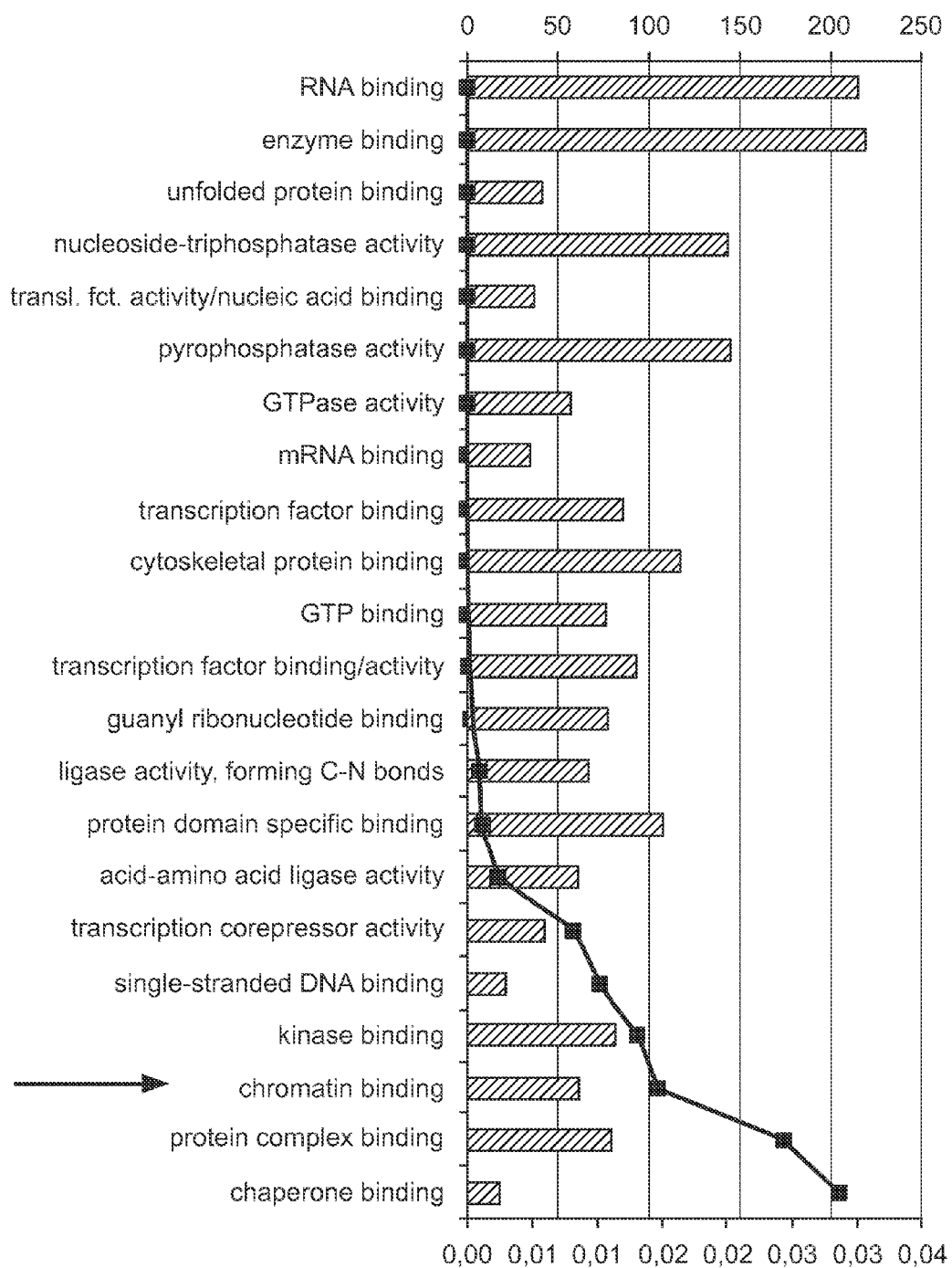
FIG. 2A is a bar graph showing the results of a global gene expression analysis in miR reprogrammed cardiac fibroblasts. Gene affiliation analysis led to the identification of 22 significant terms for molecular function of genes found changed in microarray 9 days post miR transfection. 62 of these genes affect chromatin binding.

Direct conversion of injured cardiac tissue to functional cardiomyocytes in situ is clinically useful to induce cardiac repair and/or regeneration. Combinations of microRNAs (miRs), e.g., -1, -133, -208 and -499, were found to reprogram mouse cardiac fibroblasts in vitro and in vivo to cardiomyocyte and cardiomyocyte-like cells (Jayawardena et al., Circ Res, 2012, 110:1465-1473 and PCT/US2011/043438; both references are hereby incorporated by reference).

Studies were carried out to investigate the mechanisms involved in the process of miR mediated cardiac reprogramming as well as to explore the feasibility of this approach in converting human fibroblasts towards the cardiomyocyte fate. Histone methyltransferase activity was found to play a role in miR mediated cardiac reprogramming.

Cardiac Reprogramming

Somatic cells have been reprogrammed to an embryonic-like state via viral transfection of four pluripotency factors (Takahashi et al., 2006, Cell 126, 663-676). Transcription factors have also been used to induce cellular reprogramming. A specific combination of three transcription factors (Zhou et al., 2008, Nature 455, 627-632) was employed to reprogram adult exocrine pancreatic cells in vivo to insulin-producing 13-cells representing the potential for switching gene expression in living organisms. Another study demonstrated that two cardiac transcription factors Gata4 and Tbx5 along with the chromatin-remodeling complex Baf60c, are capable of inducing programming and transdifferentiation of embryonic mouse mesoderm (Takeuchi et al., 2009, Nature 459, 708-711) to beating heart tissue. The central premise underlying the majority of these studies is the use of key transcription factors overexpression to redirect or control cell fate. The methods described herein preferably do not involve the use of transcription factors.

Alternative methods for reprogramming cells have been studied to identify viable methods for directly reprogramming cells without an intermediary stem cell-like state, to circumvent the potential complications associated with differentiating the reprogrammed stem cells to the appropriate differentiated cell type of tissue. A previous study elucidated the role for microRNAs as a therapeutic to activate key molecular programs for directly reprogramming non-cardiomyocytic cells, i.e., fibroblasts, to functional cardiomyocytic tissue (Jayawardena et al., Circ Res, 2012, 110:1465-1473; hereby incorporated by reference in its entirety). Transient overexpression of the combination of mir-1, mir-133, mir-208 and mir-499 results in early induction of cardiac mesoderm and committed cardiac progenitor markers in both murine and human fibroblasts, as well as increased cardiac function, thereby indicating reprogramming of the cells.

The compositions and methods described herein are based on the surprising discovery that histone methyltransferases play a critical role in miR-mediated cardiac reprogramming. Modulators of histone methyltransferase activity were found to induce expression of cardiac markers and cardiac function in fibroblast cells.

The approaches described herein is particularly suitable for treatment of cardiovascular conditions where there is a significant need to improve cardiac repair and remodeling in acquired heart disease. For example, one application of the compositions described herein is administration of the present composition to the fibrotic tissue in diseased or damaged hearts for direct reprogramming of the cardiac fibroblasts or other cells in the fibrotic tissue to functional cardiomyocytes or cardiomyocytic progenitor cells. In this approach, fibrotic tissue that impairs cardiac function is converted to functional cardiac tissue, to improve cardiac function.

Histone Methyltransferases

Histone methylation plays an important role in inheritable changes in expression of genes that are not based on changes at the DNA level. Specifically, histone methylation plays an important role on the assembly of the heterochromatin mechanism and the maintenance of gene boundaries between genes that are transcribed and those that are not. This process is highly controlled because changes in gene expression patterns can profoundly affect fundamental cellular processes, such as differentiation, proliferation and apoptosis.

In eukaryotic cells, DNA is packaged with histones to form chromatin, Approximately 150 base pairs of DNA are wrapped twice around an octamer of histones (two each of histones 2A, 2B, 3 and 4) to forma nucleosome, the basic unit of chromatin. The histone tails (furthest from the nueosome core) is the N-terminal end, and residues are numbered starting on this end. Control of changes in chromatin structure (and hence of transcription) is mediated by covalent modifications to histones, most notably of their N-terminal tails. Histone modifications that result in changes in gene expression include methylation, acetylation, sumoylation, phosphorylation, and ubiquitination.

The compositions and methods disclosed herein are related to modulation histone methylation. The selective addition of methyl groups to specific amino acid sites on histones is controlled by the action of a unique family of enzymes known as histone methyltransferases (HMTs). The level of expression of a particular gene is influenced by the presence or absence of one or more methyl groups at a relevant histone site. The specific effect of a methyl group at a particular histone site persists until the methyl group is removed by a histone demethylase, or until the modified histone is replaced through nucleosome turnover. Methylation of a histone can be inherited. Methylation of histones can turn the genes in the adjacent DNA "off" and "on", respectively, either by loosening or encompassing their tails, thereby allowing or blocking transcription factors and other proteins to access the DNA. This process is critical for the regulation of gene expression that allows different cells to express different portions of the genome, or specifically, tissue or cell-type specific genes.

Histones are methylated on lysine (K) and arginine (R) residues. Methylation is most commonly observed on lysine or arginine residues of histone tails of histone H3 and H4. Histones can be methylated as follows: lysine 26 on H1 (H1K26), lysine 4 on H3 (H3K4), arginine 8 on H3 (H3R8), lysine 9 on H3 (H3K9), arginine 17 on H3 (H3R17), lysine 27 on H3 (H3K27), lysine 36 on H3 (H3K36), lysine 79 on H3 (H3K79), arginine 3 on H4 (H4R3), lysine 20 on H4 (H4K20), and lysine 59 on H4 (H4K59). Preferably, the compositions and methods described herein modulate the methylation at H3K9, H3K27, and H4R3.

Histone methyltransferases are specific to either lysine or arginine. The lysine-specific transferases are further broken down into whether or not they have a SET domain or a non-SET domain. These domains specify how the enzyme catalyzes the transfer from S-adenosyl methionine to the histone residue. The methyltransferases can add 1, 2 or 3 methyls on the target residues. Examples of histone methyltransferases include, but are not limited to, Setdb2, Setd7, Setd8, Prmt7, Ezh1, Ezh2, G9a, Set 2, MLL, ALL-1, Prmt5, Prmt1, Suv38h, G9a, Setdb1, Ash1, Dot1 (Dot1L), Prmt1, Suv4-20h, Smyd3, Smyd5, and Carm1. Preferably, the inhibitors or enhancers of histone methyltransferase include Setdb2, Setd7, Setd8, Prmt7, Ezh1, and Ezh2.

Setd7 (also known as SET7, SET9, SET7/SET9, and KMT7) is a SET-domain containing lysine methyltransferase that is characterized by its methylation of lysine 4 on histone H3. The human mRNA sequence of Setd7 (Genbank Accession No. NM_030648.2) is as follows:

```
(SEQ ID NO: 1)
GGAGAAAGTTGCAGCAGCGGCAGCGGCCAAGGCGGCACACCGGAGCCTCCGAGGCGAGGGGCAAGTGGGC

GAAGGGAGGGGGACGACGGCTGCTGCCGCAGCAGCTGAAGGCCAAGGAATTGAAAGGGCTGTAGGGGGA

GGCAGTGCGAGCCAGCCCCGACTGCTCCTCCTCTTCCTCCTCCTCCAAACTCGCGAGCCCCAGAGCT

CGCTCAGCCGCCGGGAGCACCCAGAGGGACGGGAGGCAGCCGCGCAGCCCCGAGCTGGGCAGTGTCCCCA

GCCGCCATGGATAGCGACGACGAGATGGTGGAGGAGGCGGTGGAAGGGCACCTGGACGATGACGGATTAC

CGCACGGGTTCTGCACAGTCACCTACTCCTCCACAGACAGATTTGAGGGGAACTTTGTTCACGGAGAAAA

GAACGGACGGGGAAGTTCTTCTTCTTTGATGGCAGCACCCTGGAGGGGTATTATGTGGATGATGCCTTG

CAGGGCCAGGGAGTTTACACTTACGAAGATGGGGAGTTCTCCAGGGCACGTATGTAGACGGAGAGCTGA

ACGGTCCAGCCCAGGAATATGACACAGATGGGAGACTGATCTTCAAGGGGCAGTATAAAGATAACATTCG

TCATGGAGTGTGCTGGATATATTACCCAGATGGAGGAAGCCTTGTAGGAGAAGTAAATGAAGATGGGGAG

ATGACTGGAGAGAAGATAGCCTATGTGTACCCTGATGAGAGGACCGCACTTTATGGGAAATTTATTGATG

GAGAGATGATAGAAGGCAAACTGGCTACCCTTATGTCCACTGAAGAAGGGAGGCCTCACTTTGAACTGAT

GCCTGGAAATTCAGTGTACCACTTTGATAAGTCGACTTCATCTTGCATTTCTACCAATGCTCTTCTTCCA

GATCCTTATGAATCAGAAAGGGTTTATGTTGCTGAATCTCTTATTTCCAGTGCTGGAGAAGGACTTTTTT

CAAAGGTAGCTGTGGGACCTAATACTGTTATGTCTTTTTATAATGGAGTTCGAATTACACACCAAGAGGT

TGACAGCAGGGACTGGGCCCTTAATGGGAACACCCTCTCCCTTGATGAAGAAACGGTCATTGATGTGCCT

GAGCCCTATAACCACGTATCCAAGTACTGTGCCTCCTTGGGACACAAGGCAAATCACTCCTTCACTCCAA

ACTGCATCTACGATATGTTTGTCCACCCCCGTTTTGGGCCCATCAAATGCATCCGCACCCTGAGAGCAGT
```

-continued

```
GGAGGCCGATGAAGAGCTCACCGTTGCCTATGGCTATGACCACAGCCCCCCGGGAAGAGTGGGCCTGAA

GCCCCTGAGTGGTACCAGGTGGAGCTGAAGGCCTTCCAGGCCACCCAGCAAAAGTGAAAGGCCTGGCTTT

GGGGTTCAGAGACCTGGAATAGAAACTTGGATCTATGCACTACGTTTATCTGACAATGGGACAACCAGGG

ACTGCTCATGCTGTGACGTCACATCCTCTCACCATGCGTTAGCAACGACTTTCTCGCATACTAACTAGGT

TTGACTGTATTACTCATACCAGATTTAAAATTAGCTAGCCTTGCAACAACGTCCTACTGAGAGGTATTGT

CGAGCATTTGACATAAGACAGCGTGATGTTCTTTGGTGGTTCAAGTCTAAATCTGTACCACATTCGGAGA

TGCCAAATGATTAGACTGAAACAGGGAAACGGGGTTTTTCAGTCATTTTTAGTCAGTGGTTTTTCCATAG

TGCTTTTTTCCTATGGCCAGTGCAAATTGTGTTAGCACACTTGCATATGTGCCGTATTAAGGGTTGACAA

TTACTACATCTTTATTCTCTAAATGTAGTATAATTTGCCTTTTAACCTTTGATCTGTATCTTGCAATAGA

ATGGCTTTGGTTTTTTTCTTAGTAAATAGGAGCCCACTTCTAAAGTCATTTCACCCCTCAGCCCTATTCT

CTTTCTTAGATACCCTTTACAAGAGAAAACTTCCAAATGGATTTTTGCATCAATAGCAGTGTGTAGGTCT

CTCTGGTTCTTTCTATATCATCATTTTATTATTATGTCCTAATATAAAGTACTGGCTCATAGGGCCAGGG

TATTATTATAGAATATTATTCTCGCATGTAAACAAAGATATCTTTGCTTTAAGATGTGAGAAGAAATGAA

TTTACTTTGTTTGCATTAAGTTATGGAAGAGTTGTAATATATACTTTAAGAAAGAAGAGAAGAAAACTAG

TATCTCTAAGCGGTAACTATGGCAATTTTGCAATATTTTCAGTAGTGCTAGTAATTTTTTCCTCCTTGAG

TACACATTAAATGTACATAACATAGCGCGGTCAGGCTTGTGGCACAGTGCATTGAATTCAAAAGTCAAAC

AGCAAATTTGAATTCTAACAGAATTCAAAAAAAAATTTTTTTAGTCAGTACTACTAAGGCAGACACACTG

ATTACTAGGTACAAATCAAACCTTGATGCTAAAACTCTTCATCATTGTAATTTCAAAGCACTTACCTGCT

TCAAAACATTGTAAACTAAGACTGAACACCTGTATAGTTTAAAAGCAACACTATCAATAGCATTTCAGCC

ATTTTGCCAGCCATGTGTAATCACAACTGCAGAAATAAGGAGAAAACCCCTGTTTTTTTAGTTTAGCTAA

TTAGATCTGTAACATCACTGGGATTGCTCTGAATGAATCCTGAGAGTTTTGTTTTTTATAAGCACCCTCA

CCACATGCCATAGCTTTGTCTCTTTTAGACACCTCGATGCAGCGGCTGGAAGGACTGGAGAGCAGCTGTT

GTGCTGATCTGTAGCTGTCAGCTGTGATTCCTGTCACCTGAGTCAGTTTGGTCTGGAAAGCGAAGGCCTT

CCAAGCTGTAGCAGATAGTGAGCTCCAGCTGATGAGAGAAGGCTTCAGTGGAAGAAGAGTGAGGACATAG

GCAGAAGGAAGTTTGCTATTTCTTGTCAGTTGCACATTGCTTTATGAAGACTACAACAAAAGTGCTTAAT

CCCAGGCTGCTCATGACTTTCATTTCAGGTGGCCCTTGGGCACATTGACAGAGTTGCCCTTCCCTTCTTT

GCAACACCAGGCTTCCTAGAGCACCCGGTTGCATGCTTTGCAGCTAGGTGGCAGTGGTTTCAGGGAGATC

CAGTTGGATCCCTGCTTGAAAGCTTAAGCCAATGGTTCACCCATGAGAGGAAGTTGTCAGTGCTTCCAGG

AAGATTGCCCACCAAAGGAACTGAATAGTTTTTAGATTTAAAGGCACCAGGATAGGGTCACTCTTACTCT

GTAGAAAGAGACCGTTCTATACACTGTGACGGATGGGCCAGGGCCTCTGGACTTGCATTCTGATAGGTGC

TTTAATTTAAATGTGCCCAAAGGGAGTGACTGTCTTCAGGAGAAAGATGGCTTGCATTAACCTCGATCAA

GTGGGTTGTGCAGCCAGGTCAGGGAATGCGGTCAGGGAGAGGATAGTGCTGGTCATGCCCCCGATGCAGC

TATGCTCTGAATGATTTCATTCCTGAGAGTGATAGCATTCTGGTCCTGGCTGCAGTGGGGTACAATTTAC

GTCCTAAGTGGGGCTACTCTAATTATCCCATTCAAATGGAATTTTTTTCAAAATTGGATAGAAGGAATT

GAAGAGTTGTAAGTAGTGATTAGTCTGCTAATCAGTTCTTCAGATGAGATATTGAATGGTAACACTCTGA

GCTTAAAACTCAGCAGTGTGTCTGTGACCTCCACGCAAATCAGAGGAAGCAATGCATCCACGCTGAGCCT

CACCATGTCTTCCTCCCAACTCTCTTCATACTCTCTGTGTCTTCCAGCTCTTCTTTCTCGGCCGGCTCT

CTTTCCTCTTCTCTCTGCATATGTGAGAACGCCTGGGCATCCTGGGTAACAGCAGCCCCAGCTGCCCTCT

CCTGTTCCCTGTTCCAAGTCCCCTGCACTGACCTTTCTTGAGTCTCTCTGGCTCTGTGCATGTCTTTGGG

ACTCTGCTCATCTGGCTTTTCCTCTGTGTGTGCCTCTCTGTTTGCTTATGTCTCTGGCTCTGTCTTCCCC
```

-continued

```
ACCCCTCCCCTCACACACACACATACTCCCAAATGTAAGGCTCTGTGGCAGGTTGGAATCGGAGTAAGGC
TTGAGATTCACTGAGTTCTGTAGGTAGGGAAAGAAGTCAAGGGAGTGGAGGTTCTATAAGGAATTAACAG
CTGAGGACGGAAGGGTTTGTTTCCCGTTTGAACCTAAACGCAAGTGGAAAAGAATACTCAGAATGTATTT
TTCTACTTTACATCTGCTGGGGAAGGAAATGTGTCAGGAAGCCGCTGCATCTGGTCATTTCATCGCATCA
GAATCACAGCAGACGTGGAAGATTCCATGTGGTGGGGAATAAAGAAATAACTTTATGCTCTCCTGAAAAA
CAGCGGGAGCCTATGTGTGTGTGCGACACTGTAATCTCAAGGAGATTCACTCAGAGCTGTCTCAGTCCAA
CTCCTGCATGACCAGATCTTCCCTTAGCATCTTTTCTGTGATGAAATATTATCTTGTGTTAGAGTTAGGA
ATAGGAACTAACCTGTAGGAGCATGTCCCCAAATGGACATTTGAATGGACTAACAAAAACAACTGGAAAG
ACTGAATTTCCGACACAAAGGAATGATGGGATCAAAAAGAAAGCAGTGAGGAGTTCTTGAGTCTTGTAGT
ACCTATTCTTATTTTAACTTGCTTCATCCTTGATCTACCTGAGACACTAAGAAGGAAATTAGTTTTCCAA
GAGCTCTTTGAACCTGTCTAGGACTGTAGTTAAACCTATTTGCCCTATGGGGGTTCTTCACACTCGAAAA
ACTATTTCCTTATCACCAACGACCCACCCAGAAAGGCCAATGAGGCCAAATGTAACAATTTTTAACATTT
AAATATAACTATTAAAATTGCATTAATTGTGAACAGTGAATTAAAGGGTTGTCTTCTCCAGGAGACAGTA
TGTGGCACTTTTCGTAAATTTCATTTAATATATAAAAATTTAAATCACTCACTGCAACATGCATTTAAAA
TCTTCCAAGAAGGTAGAGGTATCATTTTCTGTTTTGCTTTGTTTTAAAACAGTTGCCTCAAGCTTCTGTC
TTAAGAGTAGTGACTTAGAATCCAGATATCTTTTGTTTTAGAAAAACAAGCAAAACTATGTTGCAAGACT
GACAGTTGTAATGTTTATTTGCCACAGATCAAAGGTTCACAAAGTATATCAAATTTACATCTACTTGGGG
TACCTTGATAGATTATTATTGTTTTTCTTTTATCTTTCCCTTCAGGAATTTGGAAACTCGTTGTCACTTT
TTTTAATTTTAAAAATACTAAATTGTAATAGTTTTCTTTTGCCAAATGTGTGCGTACATATTCAAAGCAA
TGAAACTATTTCAAGCCATACAACCACAGGGGTGGGAACCCTTTTCACAAATTTTAATGTGTTTGTATGT
AAATAGATGTTTGTATGAAATATTTTCATGATAGAATGAATATATTTAAATGAAGTTGAATTATTCCAGT
GCTACTTAAACACATTACAAAAATTTTGGTGAGAATTATCTGAGTCTATTGAGATGTAATGCAGATCAAT
TTTGATTTTTAAAAATCAAAAGCCTACAATAACTCTGACTCTCAGCAACTTCCTCGGCGTTGTTGCACCT
GACGTGGAGAGAGCTCGTAGGCTTCCCCAGTGCCTCAGCCGCTTCCTGGTGGAAGTTAGGTGCTAATGGA
GGTGTGTTCACCTTTTAGTGATATCACTGCAGGCCTTTGAGGGGCCTGAGAGTGAATCAGAGGCATTAGA
GACACCGGTGCAGTTATCTGGAGCACAATTTCTTTGCAGGGCAGCAGAATCAGAAGCCAGACTTGGCCAT
GTGAACCTCGAAACTCGGTTTCCCGGCCGCCATCAACCGCCACCCTTACTGCCTAGTCACACACGTCAGG
GAGGCTGCCCTCAGTGGAGTTGGGGTTGAGACCCCAGGGTGGGACTTCACAGTTTTGCCAGCAATCTCTA
CCTTCTGACTTCTGCCTCGCAGAGAGGAAGGAGAGGGGAGCATCTGGCAAGGGGCCCATTTCTCAGCACA
GTACATTTCCTGTCTCAGCTCTGGAAGACTATGCACCCAAGCACCAAACTTCCAACCAGAGAGAGAGACG
TCCTCCGATAACAAAAATCCTTGCTTCCTCTGTCTGTGACTTTACACACAGTTGTTCAAAGTTGTTAAAT
GTCAAGAGTCAATCACATCCCTAGGACATACCTCCCAACTCTCCTGACTCTTATGTTATTGAAAAAACAA
ACAAACAAAAACTCCTTTATGATGATATTCAACTTGAGTGGGGTTTTTTTTCCACTTTGGTCCTGGATAT
AATGAAATGATACATATTAGGATAAATTTTCACTGTGTATAGTAGCAATACGAACACACATGCCAATGTA
TCAACATATCTACTTGGTTACATTTTGGTTTATGATAATTAACCTTGATTCATGTATTGGGAAGCTACAG
GGACTACGTAATACCTGCTTATCACATAGGAAAATTATGTCCATGATTCTGAGCTCCCTTCTTCAAAAGT
TTCCTCCTGGGTGTTCTATGTTCTCTCTTTATCCTGAAATACATTTATTAGGTTGTGAGGTATGTTGAAG
AAGTAGAAGCCAGGGGTATGCTTTCAGCATTTATTGCAACCAAAAGTTAACCCCATCACGGTTAACGAGC
ATCTTTGGTCTCTTGTGGAATTTGAACTAAAACTATGAGCCTTATTCAATATCTATAATTCTATGATTTT
TTTAAATTATGGGAAATTAATGAAAGATGTTTACATGAATAATGTTTGCCCTTACTGTGTTATGAATGAG
TTTTTTGTAGTGTGTCTGGGTGCATGATGCAAGAGAGTAGGAAAAATGTTTCTGAAACAAAACTTGACAA
```

ATATTTGTAATGAAAGTAAATTTAAAGATTGCTATAATTGCGCTATAGAAACAATGCAAGTATTAAACAA

AATATACAATCA

The amino acid sequence of human Setd7 (Genbank Accession No. NP_085151.1) is as follows:

(SEQ ID NO: 2)
MDSDDEMVEEAVEGHLDDDGLPHGFCTVTYSSTDRFEGNEVHGEKNGRG

KEFFEDGSTLEGYYVDDALQGQGVYTYEDGGVLQGTYVDGELNGPAQEY

DTDGRLIFKGQYKDNIRHGVCWIYYPDGGSLVGEVNEDGEMTGEKIAYV

YPDERTALYGKEIDGEMIEGKLATLMSTEEGRPHFELMPGNSVYHFDKS

TSSCISTNALLPDPYESERVYVAESLISSAGEGLFSKVAVGPNTVMSFY

NGVRITHQEVDSRDWALNGNTLSLDEETVIDVPEPYNHVSKYCASLGHK

ANHSFTPNCIYDMFVHPREGPIKCIRTLRAVEADEELTVAYGYDHSPPG

KSGPEAPEWYQVELKAFQATQQK

Ezh1 (also known as Enhancer of Zeste (*Drosophila*) Homolog 1) is a lysine methyltransferase. Ezh1 is a component of the polycomb repressive complex-2 (PRC2) and mediates methylation of lysine 27 on histone H3. Ezh1 is able to mono-, di- and trimethylate lysine 27 of histone H3 to form H3K27me1, H3K27me2 and H3K27me3. The mRNA sequence for human Ezh1 (Genbank Accession No. NM_001991.3) is as follows:

(SEQ ID NO: 3)
GCGCATGCGTCCTAGCAGCGGGACCCGCGGCTCGGGATGGAGGCTGGACACCTGTTCTGCTGTTGTGTCC

TGCCATTCTCCTGAAGAACAGAGGCACACTGTAAAACCCAACACTTCCCCTTGCATTCTATAAGATTACA

GCAAGATGGAAATACCAAATCCCCCTACCTCCAAATGTATCACTTACTGGAAAAGAAAAGTGAAATCTGA

ATACATGCGACTTCGACAACTTAAACGGCTTCAGGCAAATATGGGTGCAAAGGCTTTGTATGTGGCAAAT

TTTGCAAAGGTTCAAGAAAAAACCCAGATCCTCAATGAAGAATGGAAGAAGCTTCGTGTCCAACCTGTTC

AGTCAATGAAGCCTGTGAGTGGACACCCTTTTCTCAAAAAGTGTACCATAGAGAGCATTTTCCCGGGATT

TGCAAGCCAACATATGTTAATGAGGTCACTGAACACAGTTGCATTGGTTCCCATCATGTATTCCTGGTCC

CCTCTCCAACAGAACTTTATGGTAGAAGATGAGACGGTTTTGTGCAATATTCCCTACATGGGAGATGAAG

TGAAAGAAGAAGATGAGACTTTTATTGAGGAGCTGATCAATAACTATGATGGGAAAGTCCATGGTGAAGA

AGAGATGATCCCTGGATCCGTTCTGATTAGTGATGCTGTTTTTCTGGAGTTGGTCGATGCCCTGAATCAG

TACTCAGATGAGGAGGAGGAAGGGCACAATGACACCTCAGATGGAAAGCAGGATGACAGCAAAGAAGATC

TGCCAGTAACAAGAAAGAGAAAGCGACATGCTATTGAAGGCAACAAAAAGAGTTCCAAGAAACAGTTCCC

AAATGACATGATCTTCAGTGCAATTGCCTCAATGTTCCCTGAGAATGGTGTCCCAGATGACATGAAGGAG

AGGTATCGAGAACTAACAGAGATGTCAGACCCCAATGCACTTCCCCCTCAGTGCACACCCAACATCGATG

GCCCCAATGCCAAGTCTGTGCAGCGGGAGCAATCTCTGCACTCCTTCCACACACTTTTTTGCCGGCGCTG

CTTTAAATACGACTGCTTCCTTCACCCTTTTCATGCCACCCCTAATGTATATAAACGCAAGAATAAAGAA

ATCAAGATTGAACCAGAACCATGTGGCACAGACTGCTTCCTTTTGCTGGAAGGAGCAAAGGAGTATGCCA

TGCTCCACAACCCCGCTCCAAGTGCTCTGGTCGTCGCCGGAGAAGGCACCACATAGTCAGTGCTTCCTG

CTCCAATGCCTCAGCCTCTGCTGTGGCTGAGACTAAAGAAGGAGACAGTGACAGGGACACAGGCAATGAC

TGGGCCTCCAGTTCTTCAGAGGCTAACTCTCGCTGTCAGACTCCCACAAAACAGAAGGCTAGTCCAGCCC

CACCTCAACTCTGCGTAGTGGAAGCACCCTCGGAGCCTGTGGAATGGACTGGGGCTGAAGAATCTCTTTT

TCGAGTCTTCCATGGCACCTACTTCAACAACTTCTGTTCAATAGCCAGGCTTCTGGGGACCAAGACGTGC

AAGCAGGTCTTTCAGTTTGCAGTCAAAGAATCACTTATCCTGAAGCTGCCAACAGATGAGCTCATGAACC

CCTCACAGAAGAAGAAAAGAAAGCACAGATTGTGGGCTGCACACTGCAGGAAGATTCAGCTGAAGAAAGA

TAACTCTTCCACACAAGTGTACAACTACCAACCCTGCGACCACCCAGACCGCCCCTGTGACAGCACCTGC

CCCTGCATCATGACTCAGAATTTCTGTGAGAAGTTCTGCCAGTGCAACCCAGACTGTCAGAATCGTTTCC

CTGGCTGTCGCTGTAAGACCCAGTGCAATACCAAGCAATGTCCTTGCTATCTGGCAGTGCGAGAATGTGA

CCCTGACCTGTGTCTCACCTGTGGGGCCTCAGAGCACTGGGACTGCAAGGTGGTTTCCTGTAAAAACTGC

-continued

```
AGCATCCAGCGTGGACTTAAGAAGCACCTGCTGCTGGCCCCCTCTGATGTGGCCGGATGGGGCACCTTCA
TAAAGGAGTCTGTGCAGAAGAACGAATTCATTTCTGAATACTGTGGTGAGCTCATCTCTCAGGATGAGGC
TGATCGACGCGGAAAGGTCTATGACAAATACATGTCCAGCTTCCTCTTCAACCTCAATAATGATTTTGTA
GTGGATGCTACTCGGAAAGGAAACAAAATTCGATTTGCAAATCATTCAGTGAATCCCAACTGTTATGCCA
AAGTGGTCATGGTGAATGGAGACCATCGGATTGGGATCTTTGCCAAGAGGGCAATTCAAGCTGGCGAAGA
GCTCTTCTTTGATTACAGGTACAGCCAAGCTGATGCTCTCAAGTACGTGGGGATCGAGAGGGAGACCGAC
GTCCTTTAGCCCTCCCAGGCCCCACGGCAGCACTTATGGTAGCGGCACTGTCTTGGCTTTCGTGCTCACA
CCACTGCTGCTCGAGTCTCCTGCACTGTGTCTCCCACACTGAGAAACCCCCAACCCACTCCCTCTGTAG
TGAGGCCTCTGCCATGTCCAGAGGGCACAAAACTGTCTCAATGAGAGGGAGACAGAGGCAGCTAGGGCT
TGGTCTCCCAGGACAGAGAGTTACAGAAATGGGAGACTGTTTCTCTGGCCTCAGAAGAAGCGAGCACAGG
CTGGGGTGGATGACTTATGCGTGATTTCGTGTCGGCTCCCCAGGCTGTGGCCTCAGGAATCAACTTAGGC
AGTTCCCAACAAGCGCTAGCCTGTAATTGTAGCTTTCCACATCAAGAGTCCTTATGTTATTGGGATGCAG
GCAAACCTCTGTGGTCCTAAGACCTGGAGAGGACAGGCTAAGTGAAGTGTGGTCCCTGGAGCCTACAAGT
GGTCTGGGTTAGAGGCGAGCCTGGCAGGCAGCACAGACTGAACTCAGAGGTAGACAGGTCACCTTACTAC
CTCCTCCCTCGTGGCAGGGCTCAAACTGAAAGAGTGTGGGTTCTAAGTACAGGCATTCAAGGCTGGGGA
AGGAAAGCTACGCCATCCTTCCTTAGCCAGAGAGGGAGAACCAGCCAGATGATAGTAGTTAAACTGCTAA
GCTTGGGCCCAGGAGGCTTTGAGAAAGCCTTCTCTGTGTACTCTGGAGATAGATGGAGAAGTGTTTTCAG
ATTCCTGGGAACAGACACCAGTGCTCCAGCTCCTCCAAAGTTCTGGCTTAGCAGCTGCAGGCAAGCATTA
TGCTGCTATTGAAGAAGCATTAGGGGTATGCCTGGCAGGTGTGAGCATCCTGGCTCGCTGGATTTGTGGG
TGTTTTCAGGCCTTCCATTCCCCATAGAGGCAAGGCCCAATGGCCAGTGTTGCTTATCGCTTCAGGGTAG
GTGGGCACAGGCTTGGACTAGAGAGGAGAAAGATTGGTGTAATCTGCTTTCCTGTCTGTAGTGCCTGCTG
TTTGGAAAGGGTGAGTTAGAATATGTTCCAAGGTTGGTGAGGGGCTAAATTGCACGCGTTTAGGCTGGCA
CCCCGTGTGCAGGGCACACTGGCAGAGGGTATCTGAAGTGGGAGAAGAAGCAGGTAGACCACCTGTCCCA
GGCTGTGGTGCCACCCTCTCTGGCATTCATGCAGAGCAAAGCACTTTAACCATTTCTTTTAAAAGGTCTA
TAGATTGGGGTAGAGTTTGGCCTAAGGTCTCTAGGGTCCCTGCCTAAATCCCACTCCTGAGGGAGGGGGA
AGAAGAGAGGGTGGGAGATTCTCCTCCAGTCCTGTCTCATCTCCTGGGAGAGGCAGACGAGTGAGTTTCA
CACAGAAGAATTTCATGTGAATGGGGCCAGCAAGAGCTGCCCTGTGTCCATGGTGGGTGTGCCGGGCTGG
CTGGGAACAAGGAGCAGTATGTTGAGTAGAAAGGGTGTGGGCGGGTATAGATTGGCCTGGGAGTGTTACA
GTAGGGAGCAGGCTTCTCCCTTCTTTCTGGGACTCAGAGCCCCGCTTCTTCCCACTCCACTTGTTGTCCC
ATGAAGGAAGAAGTGGGGTTCCTCCTGACCCAGCTGCCTCTTACGGTTTGGTATGGGACATGCACACACA
CTCACATGCTCTCACTCACCACACTGGAGGGCACACACGTACCCCGCACCCAGCAACTCCTGACAGAAAG
CTCCTCCCACCCAAATGGGCCAGGCCCCAGCATGATCCTGAAATCTGCATCCGCCGTGGTTTGTATTCAT
TGTGCATATCAGGGATACCCTCAAGCTGGACTGTGGGTTCCAAATTACTCATAGAGGAGAAAACCAGAGA
AAGATGAAGAGGAGGAGTTAGGTCTATTTGAAATGCCAGGGGCTCGCTGTGAGGAATAGGTGAAAAAAAA
CTTTTCACCAGCCTTTGAGAGACTAGACTGACCCCACCCTTCCTTCAGTGAGCAGAATCACTGTGGTCAG
TCTCCTGTCCCAGCTTCAGTTCATGAATACTCCTGTTCCTCCAGTTTCCCATCCTTTGTCCCTGCTGTCC
CCCACTTTTAAAGATGGGTCTCAACCCCTCCCCACCACGTCATGATGGATGGGGCAAGGTGGTGGGGACT
AGGGGAGCCTGGTATACATGCGGCTTCATTGCCAATAAATTTCATGCACTTTAAAGTCCTGTGGCTTGTG
ACCTCTTAATAAAGTGTTAGAATCCAAAAAAAAA
```

The amino acid sequence for human Ezh1 (Genbank Accession No. NP_001982.2) is as follows:

(SEQ ID NO: 4)
MEIPNPPTSKCITYWKRKVKSEYMRLRQLKRLQANMGAKALYVANFAKVQE
KTQILNEEWKKLRVQPVQSMKPVSGHPFLKKCTIESIFPGFASQHMLMRSL
NTVALVPIMYSWSPLQQNFMVEDETVLCNIPYMGDEVKEEDETFIEELINN
YDGKVHGEEEMIPGSVLISDAVFLELVDALNQYSDEEEGHNDTSDGKQDD
SKEDLPVTRKRKRHAIEGNKKSSKKQFPNDMIFSAIASMFPENGVPDDMKE
RYRELTEMSDPNALPPQCTPNIDGPNAKSVQREQSLHSFHTLFCRRCFKYD
CFLHPFHATPNVYKRKNKEIKIEPEPCGTDCFLLLEGAKEYAMLHNPRSKC
SGRRRRRHHIVSASCSNASASAVAETKEGDSDRDTGNDWASSSSEANSRCQ
TPTKQKASPAPPQLCVVEAPSEPVEWTGAEESLERVEHGTYFNNFCSIARL
LGTKICKQVFQFAVKESLILKLPTDELMNPSQKKKRKHRLWAAHCRKIQLK
KDNSSTQVYNYQPCDHPDRPCDSTCPCIMTQNFCEKFCQCNPDCQNRFPGC
RCKTQCNTKQCPCYLAVRECDPDLCLTCGASEHWDCKVVSCKNCSIQRGLK
KHLLLAPSDVAGWGTFIKESVQKNEFISEYCGELISQDEADRRGKVYDKYM
SSFLENLNNDEVVDATRKGNKIRFANHSVNPNCYAKVVMVNGDHRIGIFAK
RAIQAGEELFFDYRYSQADALKYVGIERETDVL

Ezh2 (also known as Enhancer of Zeste (*Drosophila*) Homolog 2, ENX-1, KMT6A) is a lysine methyltransferase. Ezh2 is the catalytic subunit of the polycomb repressive complex 2 (PRC2/EED-EZH2 complex) which methylates lysine 9 and lysine 27 on histone H3. Ezh2 is able to mono-, di- and trimethylate lysine 27 of histone H3 to form H3K27me1, H3K27me2 and H3K27me3. The PRC2 complex also plays a role in recruiting DNA methyltransferases. Multiple isoforms have been described, produced by alternative splicing. The compositions disclosed herein can modulate activity or expression of any of or all of the isoforms known for Ezh2. Isoform 1 is known as the canonical Ezh2 sequence. The mRNA sequence for human Ezh2 (Genbank Accession No. NM_004456.4) is as follows:

(SEQ ID NO: 5)
GGCGGCGCTTGATTGGGCTGGGGGGGCCAAATAAAAGCGATGGCGATTGGGCTGCCGCGTTTGGCGCTCG
GTCCGGTCGCGTCCGACACCCGGTGGGACTCAGAAGGCAGTGGAGCCCCGGCGGCGGCGGCGGCGCG
CGGGGGCGACGCGCGGGAACAACGCGAGTCGGCGCGCGGGACGAAGAATAATCATGGGCCAGACTGGGAA
GAAATCTGAGAAGGGACCAGTTTGTTGGCGGAAGCGTGTAAAATCAGAGTACATGCGACTGAGACAGCTC
AAGAGGTTCAGACGAGCTGATGAAGTAAAGAGTATGTTTAGTTCCAATCGTCAGAAAATTTTGGAAAGAA
CGGAAATCTTAAACCAAGAATGGAAACAGCGAAGGATACAGCCTGTGCACATCCTGACTTCTGTGAGCTC
ATTGCGCGGGACTAGGGAGTGTTCGGTGACCAGTGACTTGGATTTTCCAACACAAGTCATCCCATTAAAG
ACTCTGAATGCAGTTGCTTCAGTACCCATAATGTATTCTTGGTCTCCCCTACAGCAGAATTTTATGGTGG
AAGATGAAACTGTTTTACATAACATTCCTTATATGGGAGATGAAGTTTTAGATCAGGATGGTACTTTCAT
TGAAGAACTAATAAAAAATTATGATGGGAAAGTACACGGGGATAGAGAATGTGGGTTTATAAATGATGAA
ATTTTTGTGGAGTTGGTGAATGCCCTTGGTCAATATAATGATGATGACGATGATGATGATGGAGACGATC
CTGAAGAAAGAGAAGAAAAGCAGAAAGATCTGGAGGATCACCGAGATGATAAAGAAAGCCGCCCACCTCG
GAAATTTCCTTCTGATAAAATTTTTGAAGCCATTTCCTCAATGTTTCCAGATAAGGGCACAGCAGAAGAA
CTAAAGGAAAAATATAAAGAACTCACCGAACAGCAGCTCCCAGGCGCACTTCCTCCTGAATGTACCCCCA
ACATAGATGGACCAAATGCTAAATCTGTTCAGAGAGAGCAAAGCTTACACTCCTTTCATACGCTTTTCTG
TAGGCGATGTTTTAAATATGACTGCTTCCTACATCGTAAGTGCAATTATTCTTTTCATGCAACACCCAAC
ACTTATAAGCGGAAGAACACAGAAACAGCTCTAGACAACAAACCTTGTGGACCACAGTGTTACCAGCATT
TGGAGGGAGCAAAGGAGTTTGCTGCTGCTCTCACCGCTGAGCGGATAAAGACCCCACCAAAACGTCCAGG
AGGCCGCAGAAGAGGACGGCTTCCCAATAACAGTAGCAGGCCCAGCACCCCCACCATTAATGTGCTGGAA
TCAAAGGATACAGACAGTGATAGGGAAGCAGGGACTGAAACGGGGGGAGAGAACAATGATAAAGAAGAAG
AAGAAGAAAGATGAAACTTCGAGCTCCTCTGAAGCAAATTCTCGGTGTCAAACACCAATAAAGATGAA
GCCAAATATTGAACCTCCTGAGAATGTGGAGTGGAGTGGTGCTGAAGCCTCAATGTTTAGAGTCCTCATT
GGCACTTACTATGACAATTTCTGTGCCATTGCTAGGTTAATTGGGACCAAAACATGTAGACAGGTGTATG
AGTTTAGAGTCAAAGAATCTAGCATCATAGCTCCAGCTCCCGCTGAGGATGTGGATACTCCTCCAAGGAA
AAAGAAGAGGGAAACACCGGTTGTGGGCTGCACACTGCAGAAAGATACAGCTGAAAAAGGACGGCTCCTCT
AACCATGTTTACAACTATCAACCCTGTGATCATCCACGGCAGCCTTGTGACAGTTCGTGCCCTTGTGTGA

-continued

```
TAGCACAAAATTTTTGTGAAAAGTTTTGTCAATGTAGTTCAGAGTGTCAAAACCGCTTTCCGGGATGCCG

CTGCAAAGCACAGTGCAACACCAAGCAGTGCCCGTGCTACCTGGCTGTCCGAGAGTGTGACCCTGACCTC

TGTCTTACTTGTGGAGCCGCTGACCATTGGGACAGTAAAAATGTGTCCTGCAAGAACTGCAGTATTCAGC

GGGGCTCCAAAAAGCATCTATTGCTGGCACCATCTGACGTGGCAGGCTGGGGGATTTTTATCAAAGATCC

TGTGCAGAAAAATGAATTCATCTCAGAATACTGTGGAGAGATTATTTCTCAAGATGAAGCTGACAGAAGA

GGGAAAGTGTATGATAAATACATGTGCAGCTTTCTGTTCAACTTGAACAATGATTTTGTGGTGGATGCAA

CCCGCAAGGGTAACAAAATTCGTTTTGCAAATCATTCGGTAAATCCAAACTGCTATGCAAAAGTTATGAT

GGTTAACGGTGATCACAGGATAGGTATTTTTGCCAAGAGAGCCATCCAGACTGGCGAAGAGCTGTTTTTT

GAT TACAGATACAGCCAGGCTGATGCCCTGAAGTATGTCGGCATCGAAAGAGAAATGGAAATCCCTTGAC

ATCTGCTACCTCCTCCCCCCTCCTCTGAAACAGCTGCCTTAGCTTCAGGAACCTCGAGTACTGTGGGCAA

TTTAGAAAAAGAACATGCAGTTTGAAATTCTGAATTTGCAAAGTACTGTAAGAATAATTTATAGTAATGA

GTTTAAAAATCAACTTTTTATTGCCTTCTCACCAGCTGCAAAGTGTTTTGTACCAGTGAATTTTTGCAAT

AATGCAGTATGGTACATTTTTCAACTTTGAATAAAGAATACTTGAACTTGTCCTTGTTGAATC
```

The amino acid sequence for human Ezh2 (Genbank Accession No. NP_04447.2) is as follows:

```
                                                    (SEQ ID NO: 13)
MGQTGKKSEKGPVCWRKRVKSEYMRLRQLKRERRADEVKSMESSNRQK

ILERTEILNQEWKQRRIQPVHILTSVSSLRGTRECSVTSDLDFPTQVI

PLKTLNAVASVPIMYSWSPLQQNFMVEDETVLHNIPYMGDEVLDQDGT

FTEELIKNYDGKVHGDRECGFINDEIFVELVNALGQYNDDDDDDGDD

PEEREEKQKDLEDHRDDKESRPPRKFPSDKIFEATSSMFPDKGTAEEL

KEKYKELTEQQLPGALPPECTPNIDGPNAKSVQREQSLHSFHTLFCRR

CFKYDCFLHRKCNYSFHATPNTYKRKNTETALDNKPCGPQCYQHLEGA

KEFAAALTAERIKTPPKRPGGRRRGRLPNNSSRPSTPTINVLESKDTD

SDREAGTETGGENNDKEEEEKKDETSSSSEANSRCQTPIKMKPNIEPP

ENVEWSGAEASMFRVLIGTYYDNECATARLIGTKTCRQVYEFRVKESS

IIAPAPAEDVDTPPRKKKRKHRLWAAHCRKIQLKKDGSSNHVYNYQPC

DHPRQPCDSSCPCVIAQNFCEKFCQCSSECQNRFPGCRCKAQCNTKQC

PCYLAVRECDPDLCLTCGAADHWDSKNVSCKNCSIQRGSKKHLLLAPS

DVAGWGIFIKDPVQKNEFISEYCGEIISQDEADRRGKVYDKYMCSFLE

NLNNDEVVDATRKGNKIRFANHSVNPNCYAKVMMVNGDHRIGIFAKRA

IQTGEELFFDYRYSQADALKYVGIEREMEIP
```

Setd8 (also known as SET8, PR-Set7, SET07) is a lysine methyltransferase. Setd8 monomethylates both histones and non-histone proteins. For example, Setd8 monomethylates lysine 20 of histone H4 (H4K20me1). The mRNA sequence for human Setd8 (Genbank Accession No. NM_020382.3) is as follows:

```
                                                    (SEQ ID NO: 14)
CTGGGTTTCCCGGGAGATCCCAGGCGGTGACAGAGTGGAGCCATGGCTA

GAGGCAGGAAGATGTCCAAGCCCCGCGCGGTGGAGGCGGCGGCGGCGGC

GGCGGCGGTGGCAGCGACGGCCCCGGGCCCGGAGATGGTGGAGCGGAGG

GGCCCGGGGAGGCCCCGCACCGACGGGGAGAACGTATTTACCGGGCAGT

CAAAGATCTATTCCTACATGAGCCCGAACAAATGCTCTGGAATGCGTTT

CCCCCTTCAGGAAGAGAACTCAGTTACACATCACGAAGTCAAATGCCAG

GGGAAACCATTAGCCGGAATCTACAGGAAACGAGAAGAGAAAAGAAATG

CTGGGAACGCAGTACGGAGCGCCATGAAGTCCGAGGAACAGAAGATCAA

AGACGCCAGGAAAGGTCCCCTGGTACCTTTTCCAAACCAAAAATCTGAA

GCAGCAGAACCTCCAAAAACTCCACCCTCATCTTGTGATTCCACCAATG

CAGCCATCGCCAAGCAAGCCCTGAAAAAGCCCATCAAGGGCAAACAGGC

CCCCCGAAAAAAGCTCAAGGAAAAACGCAACAGAATCGCAAACTTACG

GATTTCTACCCTGTCCGAAGGAGCTCCAGGAAGAGCAAAGCCGAGCTGC

AGTCTGAAGAAGGAAAAGAATAGATGAATTGATTGAAAGTGGGAAGGA

AGAAGGAATGAAGATTGACCTCATCGATGGCAAAGGCAGGGGTGTGATT

GCCACCAAGCAGTTCTCCCGGGGTGACTTTGTGGTGGAATACCACGGGG

ACCTCATCGAGATCACCGACGCCAAGAAACGGGAGGCTCTGTACGCACA

GGACCCTTCCACGGGCTGCTACATGTACTATTTTCAGTATCTGAGCAAA

ACCTACTGCGTGGATGCAACTAGAGAGACAAATCGCCTAGGAAGACTGA

TCAATCACAGCAAATGTGGGAACTGCCAAACCAAACTGCACGACATCGA

CGGCGTACCTCACCTCATCCTCATCGCCTCCCGAGACATCGCGGCTGGG

GAGGAGCTCCTGTATGACTATGGGACCGCAGCAAGGCTTCCATTGAAG

CCCACCCGTGGCTGAAGCATTAACCGGTGGGCCCCGTGCCCTCCCCGCC

CCACTTTCCCTTCTTCAAAGGACAAAGTGCCCTCAAAGGGAATTGAATT

TTTTTTTACACACTTAATCTTAGCGGATTACTTCAGATGTTTTAAAA

AGTATATTAAGATGCCTTTTCACTGTAGTATTTAAATATCTGTTACAGG

TTTCCAAGGTGGACTTGAACAGATGGCCTTATATTACCAAAACTTTTAT

ATTCTAGTTGTTTTTGTACTTTTTTTGCATACAAGCCGAACGTTTGTGC
```

-continued

```
TTCCCGTGCATGCAGTCAAAGACTCAGCACAGGTTTTAGAGGAAATAGT

CAAACATGAACTAGGAAGCCAGGTGAGTCTCCTTTCTCCAGTGGAAGAG

CCGGGACCTTCCCCCTGCACCCCCGACATCCAGGGACGGGGTGTGAGGA

AGACGCTGCCTCCCAATGGCCTGGACGGGATGTTTCCAAGCTCTTGTTC

CCCTAACGTCTCAACAGGCGCTCACTGAAGTGTATGAATATTTTTAAA

AAGGTTTTTGCAGTAAGCTAGTCTTCCCCTCTGCTTTCTCGAAAGCTTA

CTGAGCCCTGGGCCCCAAGCACGGGCCGGGCATAGATTTCCTCTTCCAC

AAGCTGCCGCTTTTCTGGGCACCTTGAAGCATCAGGGCGTGAAATCAAA

CTAGATGTGGGCAGGGAGAGGGTTGCTTACCTGCCCTGCTGGGGCAGGG

TTTCCTGAAACTGGGTTAATTCTTTATAGAAATGTGAACACTGAATTTA

TTTTAAAAAATAATAATAAAAATTTAAAAAAATTAAAAATAAAAAAAAC

CACAGAAAACAACTTTACATGTATATAGGTCTTGAAGTGAGTGAAGTGG

CTGCTTTTTTTTTTTTTTTTTTGCTTTTTTTTGCTTTTTGTAGAAGA

GATTGAGAATGGTACTCTAATCAAAAATAAAGTTTTGTAGTGGGACCAG

AAATTACTTACCTGACATCCACCCCCATTCCCCCTCATCCTGCTGGGGT

TGAAAGTTCCAGACCTGCTGTCGAGGCCTTGTGTTTGTCAGACACCCAG

TGTCCTCCTGCAAGGACGCAACTGTGAGCTGAGGTGTGAGCCTAGGAGC

CCAGGACCCCTGACCCCGGCCGCTGCTGCCAGCCTCAGAAAGGCACCCA

GGTGTGCAGGGGAGCACACAGGGCCCGGCAGCCCCCAGGAATCAAGGAT

AGGGCTAAGGTTTTCACCTTAACTGTGAAGGCAGGAGGAATAGGTGACT

GCTTCCTCCCGCCCTTCACAGAACTGATTCTCACACACTGTCCCTTCAG

TCCAGGGGGCCGGGGCTCAGGAGCCATGACCTGGTGTCTCCTGCCCACC

CTGGTCCCAGGTAAATGTGAATGGAGACAGGTATGAGAGGCTGTCCTCG

TCTTTGATTCCCCCCCAACCCCACCTCGGGCCTCACGACGGTGCTACCT

AAGAAAGTCTTCCCTCCCACCCCCCGCTAGCCTGGTCAGTGGTCAGCAA

ATTGGAAGAGGATCCGATGGGAGTGTAAATGTGAGACACAATGTCTTGA

TTATACCTGTTTGTGGTTTAGCTTTGTATTTAAACAAGGAAATAAACTT

GAAAATTATTTGTCATCATAAAAATGAAACAAATTAAAATATTTATTGC

CAGGCAAAAAAAAAAAAAAAA
```

The amino acid sequence for human Setd8 (Genbank Accession No. NP_065115.3) is as follows:

```
                                           (SEQ ID NO: 6)
MARGRKMSKPRAVEAAAAAAAVAATAPGPEMVERRGPGRPRIDGENVET

GQSKIYSYMSPNKCSGMRFPLQEENSVTHHEVKCQGKPLAGIYRKREEK

RNAGNAVRSAMKSEEQKIKDARKGPLVPFPNQKSEAAEPPKTPPSSCDS

TNAAIAKQALKKPIKGKQAPRKKAQGKTQQNRKLTDFYPVRRSSRKSKA

ELQSEERKRIDELIESGKEEGMKIDLIDGKGRGVIATKQESRGDFVVEY

HGDLIEITDAKKREALYAQDPSTGCYMYYFQYLSKTYCVDATRETNRLG

RLINHSKCGNCQTKLHDIDGVPHLILIASRDIAAGEELLYDYGDRSKAS

IEAHPWLKH
```

Setdb2 (also known as SET domain bifurcated 2, CLLd8, KMT1F, CLLL8) is a lysine methyltransferase. Setdb2 methylates histone H3, for example at lysine 9 of histone H3. Setdb2 can trimethylate lysine 9 of H3 to produce H3K9me3. The amino acid sequence for human Setdb2 (Genbank Accession No. NM_031915.2) is as follows:

```
                                           (SEQ ID NO: 7)
ATCCCCGGTAGAGGCAGGGCGGGACTGTTGTGGTTGAGATGAAGGCTAGTAAATGGTGAAGTACTTCCCG

GCCAGAGGGCACCTGCGCTCGGGAGGTTTGGGCGGCTTGGCGTCGGAGGAGAGCCCCACCCGCGGAGGAA

CCCAGCCTTGCCAACGGAGCTGGCGGAGCTCACTCCTCAGGTCAGGCGGGCGGCGTAGAAAACGCAGCGG

AGCCAGGTGAAACCAAGGCACCGCCGTGGCTGGCCCCCGACAGTTCCTCTAGCCGGGAGGTTGGAGGAGC

TGAAAACGCCGCGGAGCCCTCGGCCGCCCGAGCAGGGGCTGGACCCCAGCCCTTGCAGCCTCCCTTCTCC

TGGCACCCAAGTGCAGTCCTGGCTGCAGAAGGGGCCGCGGGCGCACTGAGTTTCCAACCTCCATTTCAGC

CTGTCTGTCTCAGGGTGCAGCCTTAATGAGAGGTGATTCCTAAGCTGCTGGGAACCTGAGGTTGTCAAAG

GGGCGGCAGGAAATGGACAGCAGTATAAAACCCAGAAGCAGAACTTGAAGGTTAAACCACTAGCCCATTT

CACAGAATGTTTCATCCATTTGTGGACCAAAAGATGGAGTTGGTTTTTATTTTTAAAAAGATAATGTTAA

TGATCTGATACCACTACAAATATTTACGTGAAGATTCATGGACTTGTCTTTTGGTTGGACTGTCACTC

ATTTCTGAAAGTTTCTTCAGCCACAATTTCTATTTGAAAATTCAAGTATCAAAGGATACCAGGTTTAGAA

TGGTATAATGATGTATTTTGTCTGAGGACTGCAAATTTTATAGAGACCACAGTTGGATTCCAGTGATATT

CTGCAATCAAAGTGATTTGATAAACCTAATTTTGAAGCATTTTATATTTATAAGCGACATCAAAAGATGG

GAGAAAAAAATGGCGATGCAAAAACTTTCTGGATGGAGCTAGAAGATGATGGAAAAGTGGACTTCATTTT

TGAACAAGTACAAAATGTGCTGCAGTCACTGAAACAAAAGATCAAAGATGGGTCTGCCACCAATAAAGAA

TACATCCAAGCAATGATTCTAGTGAATGAAGCAACTATAATTAACAGTTCAACATCAATAAAGGGAGCAT

CACAGAAAGAAGTGAATGCCCAAAGCAGTGATCCTATGCCTGTGACTCAGAAGGAACAGGAAAACAAATC
```

-continued

```
CAATGCATTTCCCTCTACATCATGTGAAAACTCCTTTCCAGAAGACTGTACATTTCTAACAACAGAAAAT
AAGGAAATTCTCTCTCTTGAAGATAAAGTTGTAGACTTTAGAGAAAAAGACTCATCTTCGAATTTATCTT
ACCAAAGTCATGACTGCTCTGGTGCTTGTCTGATGAAAATGCCACTGAACTTGAAGGGAGAAAACCCTCT
GCAGCTGCCAATCAAATGTCACTTCCAAAGACGACATGCAAAGACAAACTCTCATTCTTCAGCACTCCAC
GTGAGTTATAAAACCCCTTGTGGAAGGAGTCTACGAAACGTGGAGGAAGTTTTTCGTTACCTGCTTGAGA
CAGAGTGTAACTTTTTATTTACAGATAACTTTTCTTTCAATACCTATGTTCAGTTGGCTCGGAATTACCC
AAAGCAAAAGAAGTTGTTTCTGATGTGGATATTAGCAATGGAGTGGAATCAGTGCCCATTTCTTTCTGT
AATGAAATTGACAGTAGAAAGCTCCCACAGTTTAAGTACAGAAAGACTGTGTGGCCTCGAGCATATAATC
TAACCAACTTTTCCAGCATGTTTACTGATTCCTGTGACTGCTCTGAGGGCTGCATAGACATAACAAATG
TGCATGTCTTCAACTGACAGCAAGGAATGCCAAAACTTCCCCCTTGTCAAGTGACAAAATAACCACTGGA
TATAAATATAAAAGACTACAGAGACAGATTCCTACTGGCATTTATGAATGCAGCCTTTTGTGCAAATGTA
ATCGACAATTGTGTCAAAACCGAGTTGTCCAACATGGTCCTCAAGTGAGGTTACAGGTGTTCAAAACTGA
GCAGAAGGGATGGGGTGTACGCTGTCTAGATGACATTGACAGAGGGACATTTGTTTGCATTTATTCAGGA
AGATTACTAAGCAGAGCTAACACTGAAAAATCTTATGGTATTGATGAAAACGGGAGAGATGAGAATACTA
TGAAAAATATATTTTCAAAAAAGAGGAAATTAGAAGTTGCATGTTCAGATTGTGAAGTTGAAGTTCTCCC
ATTAGGATTGGAAACACATCCTAGAACTGCTAAAACTGAGAAATGTCCACCAAAGTTCAGTAATAATCCC
AAGGAGCTTACTGTGGAAACGAAATATGATAATATTTCAAGAATTCAATATCATTCAGTTATTAGAGATC
CTGAATCCAAGACAGCCATTTTTCAACACAATGGGAAAAAAATGGAATTTGTTTCCTCGGAGTCTGTCAC
TCCAGAAGATAATGATGGATTTAAACCACCCCGAGAGCATCTGAACTCTAAAACCAAGGGAGCACAAAAG
GACTCAAGTTCAAACCATGTTGATGAGTTTGAAGATAATCTGCTGATTGAATCAGATGTGATAGATATAA
CTAAATATAGAGAAGAAACTCCACCAAGGAGCAGATGTAACCAGGCGACCACATTGGATAATCAGAATAT
TAAAAAGGCAATTGAGGTTCAAATTCAGAAACCCCAAGAGGGACGATCTACAGCATGTCAAAGACAGCAG
GTATTTTGTGATGAAGAGTTGCTAAGTGAAACCAAGAATACTTCATCTGATTCTCTAACAAAGTTCAATA
AAGGGAATGTGTTTTTATTGGATGCCACAAAAGAAGGAAATGTCGGCCGCTTCCTTAATCATAGTTGTTG
CCCAAATCTCTTGGTACAGAATGTTTTTGTAGAAACACACAACAGGAATTTTCCATTGGTGGCATTCTTC
ACCAACAGGTATGTGAAAGCAAGAACAGAGCTAACATGGGATTATGGCTATGAAGCTGGGACTGTGCCTG
AGAAGGAAATCTTCTGCCAATGTGGGGTTAATAAATGTAGAAAAAAAATATTATAAATATGTAACTAACG
CCTGTTTGTGAAATTAGCTTATCAGGCTGAAATTAAAGCCATGCAAAAGAAGGTCTAGGTCCATCAAGGA
AATTCCCCTCCGTTTTCCTTTGTCATGGGGTTTATGTTTTATTTCAGATTTTATTTGTGTGACTTAGAAA
TTCCAGGAACACAATTAGGATATTTTCATACACATAGGGTATCTTGTTCACTGCTGTGCTACTTTACATG
AGTAGGATGAAGTGTATATTTTATATGAAATACCACTGTACAATTTATAATTTATTTACAAATTATATA
TTAAGAGAAACAAATGTCATAACAGAACTCAGCTGTTTCTAATTGCTTTTGTGACTGTTACCTTTTAGTT
CATGCCCCCCAAAGAGCTAAATTTCACATTTTTACCTACAAAATTGATTTTTAATTCCTGGCAAATAAT
TTACCATTATGAGCTACAAGGTGGGCAACAGCGCCTGAGGATCTAATTTTATGCATATTACTCCCAAGTA
TTTTAACACTTGTTGGAGAAGCAATATCTGGATCGATAAAACACTGTCCCATCAACCATTTGAGTGGGGA
GAGGGAGAAGCTCTTCTGTAAGTAAGATTCTGGCAAGCTCTTTGAAATGAGTCTTCTTTCCCACAGATTT
TCTCTACTCTTTCTATACAAACAGATAGGAGAAGAGGGAATAGAAACCTGGAGGAACTTGAATATTTTG
TTCTAGATAGAGATACAGTTACTGAAAAGGAAACCTAGAAAGTAGTCACACGTTGCTTATTTAGGCCAGA
AGTAATTGTACTGGGCAAAAATTTCACTTAAAAAACACAAGAAGTCCAGGTATGGTGGCTCAGACCTGTA
ATCCCAGCACTTTGAGAGGCCGAGGCAGGTGGATTACTTGAGCCTAGGGGTTCAAGACCAGCTTGGGCAA
```

```
CATGTCAAAACCCTGTCTCTACAAAAAATACAAAAATTAGCCTGGCATGATGGCATGTGCCCGTAGTCTC

AGCTACTCAGGAGTGAGGTGGGAGGATCATTTGAGCTCAGAAGGTCAAGGCTGCAATGAGACATAATTTC

ACCATAGTACTTCCAGCCTGGGCAATAGAGCAAGACTCTCTCTCAAAAAAAACAGCACACACACACACAC

ACGAAAACAATTCTGAACTATGAAATCTGAAACAGCCCCTTGGTATCTCCTGGGCATGATTTGCAAATCT

TTTTTTTTTACAGAAAAAAGGCAAAGAGTAAGCACTTTGCCATAGGTTACTTGGCCGTGATCATCTATCT

AGTGGAAAAGGGGACTGGGAAGCCCAAGCAGACTGGGAAACCAGACAGCTAGGAAAAGGAGCAAAACATA

GCCCAGCAACCTACAGATGAAGAAAGTTGAGAAATCCATTTATTCACCATAGAGACGCAGGAATTTCAGG

CAATGCACTAAAATGAAATGGGGGAAAAAAGCTTGATCAGTATGGGAACCATTTTTGTGCAAAAGGGAAT

ATTATGGATCAGCCAGTATTTCTTTGAGCTCTGCCTGTGGAGTCCATTTGACCTTTAGAAATATGAGGTA

TTCTGTCAGTTTTATCTTCTTGGAGAAATTTCTCCTAAAATCTTGATTTGCTTTAGTCTGGACTGGTTCA

TAGCCATCATCTTCCATCAGTACCCCAGAGATTCACTTTGTCTCTTATGTGGGATCTGTTTCCAGTTAGA

TGCCATTATTTTCCTTTTCCTTGGTTTACTCTTCCACATATTGGTAAAGCTCTTCCAATAGCTTTTGGAA

AGGAAAAATGAAAGTAAATGTTTTGAATCTCTGTGTGTTTGACAATGTCTTTATTTTACCCTTATACCT

GATTGCTGTTTTGGTTGGCAAGGTATAGGATTCTTTAGTGGTCTCCATGCCCAGTTTTGAAGACATCTGC

TAGCTTTCAGTGCTGTTGCTGTGGAGTCTGAAAATCTGTCTTCTGGCTTCCAGGGTGACTACTGGAAATT

GAATGCCATTCTGTTCCTTCTCTTTTGCATATATAATCCATTTTTATCTCTCTTGAAGCTTATAGGTTTA

TCTTTGTCTCAATGTTCTGTCCCTGTTAAGAGTCCATTTTCATCCTTTGTACTAGGTGCCTGGTGGGATC

ATTCCGTCTGAAACTAATGATTTCCCATCTCTTCACTGTTTCTGGAATTCCTGTTTTCCAGATGTTAGAC

CTCCAGAATTTGATCTCTAATTTTCCTATCTTTTCTCTTAACTTTCAGCTCTGTCTTCTTGCTAGGACCT

TTTCCTAGGAGCATTTCTCAATTTAATCTTCCAGTTCATCTGTTGCATTTTATTTTTCTAGTCTCATATT

GTCTCATATTTTAATTTCTAAGAGCTCCCCTTCTCCGAATATTCTTTTTTTTTAATAGCATCCTATTTT

GGCTCATGGTTGCAGTATTTTATCTCCTTGAAGATGTTTGTGTGTTTATGTATGTATATGCACACACGTA

TACATACACATACAGGCATGCATCTCTGTATTCTTTCGGCATAATCTGTGTCCTCCAGGGTTTGTTTCTT

TGTTTCCCCTGTATGTTTGTTTTGGTCGTTCACATTATAGGCTTTCCTCAGAGTTAATGGTCTTGGTAGT

CTACTCATATTTAAGTGTGGAACACCAAAAAGCTTACTATAAGCTGAGAGTGTGGTAAAGGGCTCTTTGT

TTTACTATGACCTACCTGAGCTATCTTGCTGGGGAACACCCTAATGTCAGTCTCTTTATAAAGGGCCTTT

CATTTTGGCCTGGCAAGAAATACTCTTTCATCCTCCTGCATGGAGGGCAAAAAAAAATTTAAAAATTGGC

TGCTAGGGTCTGTCTGCTCACTTCCCTGTTTTGCAGACCCCACACTCTTCTGCAATTCATTTCATAGTTG

TCAAGACTATACAAATTGTCCTTTTTAATGTTCTCTCTTCTGCTATCCCTAGTTGGCAGTCTTCCTCTTT

ACAACCTGCTGAAAGTGGAAGACCTCCAGTTTTCCTTTAATTCCTCAGCAAACCACCAACTATTATATGT

CTTTTTTCCAGAACAACTTATTTTTTAACTATAATTATATGCATTTATGTTAGATTCACTGAAAACCTCA

TCTTGTATGGTGCTCTGTACCCTATGGGTGCTAAATAAAGGCTTGCTACTGGCAACTGGAAAAAAAAAA

AAAAAA
```

The amino acid sequence for human Setdb2 (Genbank Accession No. NP_114121.2) is as follows:

(SEQ ID NO: 8)

MGEKNGDAKTFWMELEDDGKVDFIFEQVQNVLQSLKQKIKDGSATNKEY

IQAMILVNEATIINSSTSIKGASQKEVNAQSSDPMPVTQKEQENKSNAF

PSTSCENSFPEDCTFLTTENKEILSLEDKVVDFREKDSSSNLSYQSHDC

SGACLMKMPLNLKGENPLQLPIKCHFQRRHAKTNSHSSALHVSYKTPCG

RSLRNVEEVFRYLLETECNFLFTDNFSFNTYVQLARNYPKQKEVVSDVD

ISNGVESVPISFCNEIDSRKLPQFKYRKTVWPRAYNLTNESSMFTDSCD

CSEGCIDITKCACLQLTARNAKTSPLSSDKITTGYKYKRLQRQIPTGIY

ECSLLCKCNRQLCQNRVVQHGPQVRLQVEKTEQKGWGVRCLDDIDRGTF

VCIYSGRLLSRANTEKSYGIDENGRDENTMKNIFSKKRKLEVACSDCEV

EVLPLGLETHPRTAKTEKCPPKFSNNPKELTVETKYDNISRIQYHSVIR

```
DPESKTAIFQHNGKKMEFVSSESVTPEDNDGFKPPREHLNSKTKGAQKD

SSSNHVDEFEDNLLIESDVIDITKYREETPPRSRCNQATTLDNQNIKKA

IEVQIQKPQEGRSTACQRQQVFCDEELLSETKNTSSDSLTKFNKGNVEL

LDATKEGNVGRELNHSCCPNLLVQNVEVETHNRNFPLVAFFTNRYVKAR

TELTWDYGYEAGTVPEKEIFCQCGVNKCRKKIL
```

PRMT7 (also known as protein arginine methyltransferase 7, KIAA1933, and FLJ10640) is an arginine methyltransferase. PRMT7 can methylate arginine 3 on histone H4 (H4R3), for example dimethylation of arginine 3 on H4 to produce H4R3me2. The mRNA sequence for human PRMT7 (Genbank Accession No. NM_019023.2) is as follows:

```
                                        (SEQ ID NO: 9)
AGCTTTCCAGTTCTGCTTTAGGACCCGCCCCCCAGCACGCTCCTCGACG

CTGCGAGGTCCCGCCCCGCGTGCTGGCGCGGTAAAAGTGGTAGCAGCG

GAGGCGAGCGGAGGGTTTCCCGCGGCGGAGTCTCACTCTGCTGCCTAGG

CTGAGTGCAGTGGTGTGATCGAGGCGCACTGCAGCCTTGACCTCCTGGG

CTCAAGCGATCCTCACCTCGGCCTACCGAGTAGCTGGGACTACAGGCAC

GCGCCACTACACTCGGATTTCTGACAGTCAGACTTGTCCACAAGAACTC

AACTGGCAAGGCTGCTTTTCTGTGCTAAAACTGGGGAGCTAGTGGGCAC

CATGAAGATCTTCTGCAGTCGGGCCAATCCGACCACGGGGTCTGTGGAG

TGGCTGGAGGAGGATGAACACTATGATTACCACCAGGAGATTGCAAGGT

CATCTTATGCAGATATGCTACATGACAAAGACAGAAATGTAAAATACTA

CCAAGGTATCCGGGCTGCCGTGAGCAGGGTGAAGGACAGAGGACAGAAG

GCCTTGGTTCTCGACATTGGCACTGGCACGGGACTCTTGTCAATGATGG

CGGTCACAGCAGGTGCCGACTTCTGCTATGCCATCGAGGTTTTCAAGCC

TATGGCTGATGCTGCTGTGAAGATTGTGGAGAAAAATGGCTTTAGTGAT

AAGATTAAGGTTATCAACAAGCATTCCACCGAGGTGACTGTAGGTCCAG

AGGGTGACATGCCATGCCGTGCCAACATCCTGGTCACAGAGTTGTTTGA

CACAGAGCTGATCGGGGAGGGGCGCTGCCCTCCTATGAGCACGCACAC

AGGCATCTCGTGGAGGAAAATTGTGAGGCCGTGCCCCACAGAGCCACCG

TCTATGCACAGCTGGTGGAGTCCGGGAGGATGTGGTCGTGGAACAAGCT

ATTTCCCATCCACGTGCAGACCAGCCTCGGAGAGCAGGTCATCGTCCCT

CCCGTTGACGTGGAGAGCTGCCCTGGCGCACCCTCTGTCTGTGACATTC

AGCTGAACCAGGTGTCACCAGCCGACTTTACAGTCCTCAGCGATGTGCT

GCCCATGTTCAGCATAGACTTCAGCAAGCAAGTCAGTAGCTCAGCAGCC

TGCCATAGCAGGCGGTTTGAACCTCTGACATCTGGCCGAGCTCAGGTGG

TTCTCTCGTGGTGGGACATTGAAATGGACCCTGAGGGGAAGATCAAGTG

CACCATGGCCCCCTTCTGGGCACACTCAGACCCAGAGGAGATGCAGTGG

CGGGACCACTGGATGCAGTGTGTGTACTTCCTGCCACAAGAGGAGCCTG

TGGTGCAGGGCTCAGCGCTCTATCTGGTAGCCCACCACGATGACTACTG

CGTATGGTACAGCCTGCAGAGGACCAGCCCTGAAAAGAATGAGAGAGTC

CGCCAGATGCGCCCCGTGTGTGACTGCCAGGCTCACCTGCTCTGGAACC

GGCCTCGGTTTGGAGAGATCAATGACCAGGACAGAACTGATCGATACGT

CCAGGCTCTGAGGACCGTGCTGAAGCCAGACAGCGTGTGCCTGTGTGTC

AGCGATGGCAGCCTGCTCTCCGTGCTGGCCCATCACCTGGGGGTGGAGC

AGGTGTTTACAGTCGAGAGTTCAGCAGCTTCTCACAAACTGTTGAGAAA

AATCTTCAAGGCTAACCACTTGGAAGATAAAATTAACATCATAGAGAAA

CGGCCGGAATTATTAACAAATGAGGACCTACAGGGCAGAAAGGTCTCTC

TCCTCCTGGGCGAGCCGTTCTTCACTACCAGCCTGCTGCCGTGGCACAA

CCTCTACTTCTGGTACGTGCGGACCGCTGTGGACCAGCACCTGGGGCCA

GGTGCCATGGTGATGCCCCAGGCAGCCTCGCTGCACGCTGTGGTTGTGG

AGTTCAGGGACCTGTGGCGGATCCGGAGCCCCTGTGGTGACTGCGAAGG

CTTCGACGTGCACATCATGGACGACATGATTAAGCGTGCCCTGGACTTC

AGGGAGAGCAGGGAAGCTGAGCCCCACCCGCTGTGGGAGTACCCATGCC

GCAGCCTCTCCGAGCCCTGGCAGATCCTGACCTTTGACTTCCAGCAGCC

GGTGCCCCTGCAGCCCCTGTGTGCCGAGGGCACCGTGGAGCTCAGAAGG

CCCGGGCAGAGCCACGCAGCGGTGCTATGGATGGAGTACCACCTGACCC

CGGAGTGCACGCTCAGCACTGGCCTCCTGGAGCCTGCAGACCCCGAGGG

GGGCTGCTGCTGGAACCCCACTGCAAGCAGGCCGTCTACTTCTTCAGC

CCTGCCCCAGATCCCAGAGCACTGCTGGGTGGCCCACGGACTGTCAGCT

ATGCAGTGGAGTTTCACCCCGACACAGGCGACATCATCATGGAGTTCAG

GCATGCAGATACCCCAGACTGACCACTCTTGAGCAATAAAGTGGCCTGA

GGGCTGGGGTTCTGAAAAAAAAAAAAAA
```

The amino acid sequence for human PRMT7 (Genbank Accession No. NP_061896.1) is as follows:

```
                                        (SEQ ID NO: 10)
MKIFCSRANPTTGSVEWLEEDEHYDYHQEIARSSYADMLHDKDRNVKY

YQGIRAAVSRVKDRGQKALVLDIGTGTGLLSMMAVTAGADFCYAIEVE

KPMADAAVKIVEKNGESDKIKVINKHSTEVTVGPEGDMPCRANILVTE

LFDTELIGEGALPSYEHAHRHLVEENCEAVPHRATVYAQLVESGRMWS

WNKLFPIHVQTSLGEQVIVPPVDVESCPGAPSVCDIQLNQVSPADFTV

LSDVLPMFSIDFSKQVSSSAACHSRRFEPLTSGRAQVVLSWWDIEMDP

EGKIKCTMAPFWAHSDPEEMQWRDHWMQCVYFLPQEEPVVQGSALYLV

AHHDDYCVWYSLQRTSPEKNERVRQMRPVCDCQAHLLWNRPREGEIND

QDRTDRYVQALRTVLKPDSVCLCVSDGSLLSVLAHHLGVEQVFTVESS

AASHKLLRKIFKANHLEDKINIIEKRPELLTNEDLQGRKVSLLLGEPF

ETTSLLPWHNLYFWYVRTAVDQHLGPGAMVMPQAASLHAVVVEFRDLW

RIRSPCGDCEGFDVHIMDDMIKRALDFRESREAEPHPLWEYPCRSLSE

PWQILTFDFQQPVPLQPLCAEGTVELRRPGQSHAAVLWMEYHLTPECT

LSTGLLEPADPEGGCCWNPHCKQAVYFFSPAPDPRALLGGPRTVSYAV

EFHPDTGDIIMEFRHADTPD
```

Aurora kinase b (also known as Aurkb, STK5, STK12, AurB, Auror-1, Aurora-B) is a serine/threonine protein kinase that is known to have effect on histone methylation.

Compositions and methods disclosed herein also include compositions that comprise inhibitors or enhancers of Aurkb. Multiple transcript variants encoding different isoforms have been found, and include Genbank Accession Nos. NM_001256834.1, NM_NM_004217.3, NP_001243763, and NP_004208.2; each of which are hereby incorporated by reference). An exemplary mRNA sequence of human Aurkb (Genbank Accession Nos. NM_NM_004217.3) is as follows:

(SEQ ID NO: 11)
CGGGGCGGGAGATTTGAAAAGTCCTTGGCCAGGGCGCGGCGTGGCAGAT

TCAGTTGTTTGCGGGCGGCCGGGAGAGTAGCAGTGCCTTGGACCCCAGC

TCTCCTCCCCCTTTCTCTCTAAGGATGGCCCAGAAGGAGAACTCCTACC

CCTGGCCCTACGGCCGACAGACGGCTCCATCTGGCCTGAGCACCCTGCC

CCAGCGAGTCCTCCGGAAAGAGCCTGTCACCCCATCTGCACTTGTCCTC

ATGAGCCGCTCCAATGTCCAGCCCACAGCTGCCCCTGGCCAGAAGGTGA

TGGAGAATAGCAGTGGGACACCCGACATCTTAACGCGGCACTTCACAAT

TGATGACTTTGAGATTGGGCGTCCTCTGGGCAAAGGCAAGTTTGGAAAC

GTGTACTTGGCTCGGGAGAAGAAAAGCCATTTCATCGTGGCGCTCAAGG

TCCTCTTCAAGTCCCAGATAGAGAAGGAGGGCGTGGAGCATCAGCTGCG

CAGAGAGATCGAAATCCAGGCCCACCTGCACCATCCCAACATCCTGCGT

CTCTACAACTATTTTTATGACCGGAGGAGGATCTACTTGATTCTAGAGT

ATGCCCCCCGCGGGGAGCTCTACAAGGAGCTGCAGAAGAGCTGCACATT

TGACGAGCAGCGAACAGCCACGATCATGGAGGAGTTGGCAGATGCTCTA

ATGTACTGCCATGGGAAGAAGGTGATTCACAGAGACATAAAGCCAGAAA

ATCTGCTCTTAGGGCTCAAGGGAGAGCTGAAGATTGCTGACTTCGGCTG

GTCTGTGCATGCGCCCTCCCTGAGGAGGAAGACAATGTGTGGCACCCTG

GACTACCTGCCCCCAGAGATGATTGAGGGGCGCATGCACAATGAGAAGG

TGGATCTGTGGTGCATTGGAGTGCTTTGCTATGAGCTGCTGGTGGGGAA

CCCACCCTTTGAGAGTGCATCACACAACGAGACCTATCGCCGCATCGTC

AAGGTGGACCTAAAGTTCCCCGCTTCCGTGCCCATGGGAGCCCAGGACC

TCATCTCCAAACTGCTCAGGCATAACCCCTCGGAACGGCTGCCCCTGGC

CCAGGTCTCAGCCCACCCTTGGGTCCGGGCCAACTCTCGGAGGGTGCTG

CCTCCCTCTGCCCTTCAATCTGTCGCCTGATGGTCCCTGTCATTCACTC

GGGTGCGTGTGTTTGTATGTCTGTGTATGTATAGGGGAAAGAAGGGATC

CCTAACTGTTCCCTTATCTGTTTTCTACCTCCTCCTTTGTTTAATAAAG

GCTGAAGCTTTTTGTACTCATGAAAAAAAAAAAAAAAAA

An exemplary amino acid sequence of human Aurkb (Genbank Accession Nos. NM_NM_004208.2) is as follows:

(SEQ ID NO: 12)
MAQKENSYPWPYGRQTAPSGLSTLPQRVLRKEPVTPSALVLMSRSNVQP

TAAPGQKVMENSSGTPDILTRHETIDDFEIGRPLGKGKEGNVYLAREKK

SHFIVALKVLEKSQIEKEGVEHQLRREIEIQAHLHHPNILRLYNYFYDR

RRIYLILEYAPRGELYKELQKSCTEDEQRTATIMEELADALMYCHGKKV

-continued
IHRDIKPENLLLGLKGELKIADFGWSVHAPSLRRKTMCGTLDYLPPEMI

EGRMHNEKVDLWCIGVLCYELLVGNPPFESASHNETYRRIVKVDLKFPA

SVPMGAQDLISKLLRHNPSERLPLAQVSAHPWVRANSRRVLPPSALQSV

A

Modulators of Histone Methyltransferases

Modulators of histone methylation include inhibitors of histone methyltransferases and enhancers of histone methyltransferases. Modulators disclosed herein can inhibit or enhance the activity of any of the histone methyltransferases disclosed herein, preferably Setdb2, Setd7, Setd8, Prmt7, Ezh1, Ezh2, or Aurkb. Modulators disclosed herein can increase or decreased expression of any of the histone methyltransferases disclosed herein, preferably Setdb2, Setd7, Setd8, Prmt7, Ezh1, Ezh2, or Aurkb.

Examples of small molecule inhibitors of histone methyltransferases are described below. Such inhibitors can target both lysine and arginine methyltransferases, for example, those disclosed in WO 2013/063417 (the contents of which are hereby incorporated by reference in its entirety). S-adenosyl-methionine (SAM) analog inhibitors are broadly inhibiting to methyltransferases, as they are analogs of the methyl substrate, and therefore competitively inhibit methyltransferases. Examples of SAM analogs include, but are not limited to EPZ004777 (CAS 1338466-77-5; BioVision Incorporated).

Small molecule inhibitors of lysine histone methyltransferases include BTX 01294 (also known as 2-(Hexahydro-4-methyl-1H-1,4-diazepin-1-yl)-6,7-dimethoxy-N-[1-(phenylmethyl)-4-piperidinyl]-4-quinazolinamine trihydrochloride hydrate; Tocris Biosciences)) (and its derivative TM2-115), 3-Deazaneplanocin A hydrochloride (DZnep) (Tocris Biosciences), chaetocin (CAS 28094-03-2; Tocris Biosciences; Sigma-Aldrich), SGC 0946 (Tocris Biosciences, Selleck Chemicals), UNC 0224 (CAS 1197196-48-7; Tocris Biosciences, Cayman Chemical), UNC 0638 (CAS 1255517-77-1; Tocris Bioscience), UNC 0646 (CAS 1320288-17-2; Tocris Biosciences), 2-cyclohexyl-N-(1-isopropylpiperidin-4-yl)-6-methoxy-7-(3-(pyrrolidin-1-yl) propoxy) quinazolin-4-amine, polyhydroxy derivatives of (2,3,7,8-tetrahydroxy[1]benzopyrano (5,4,3(de)[1]benzopyran5,10-dione) (for example, those disclosed in WO2008/001391). Inhibitors of Ezh2 include S-adenosyl-L-homocysteine and analogs or derivatives thereof (for example, those disclosed in WO2012/034132; hereby incorporated by reference in its entirety).

BIX-01294 (trihydrochloride hydrate) (2-(Hexahydro-4-methyl-1H-1,4-diazepin-1-yl)-6,7-dimethoxy-N-[1-(phenylmethyl)-4-piperidinyl]-4-quinazolinamine trihydrochloride; Tocris Biosciences) is a diazepin-quinazolinamine derivative. This inhibitor is a lysine methyltransferase inhibitor, and does not compete with cofactor S-adenosylmethionine. Specifically, BIX-01294 has been shown to inhibit methylation at lysine 9 of histone H3 (H3K9). Reported activity includes inhibition of dimethylation of H3K9 (H3K9me2), and inhibition of G9a-like protein and G9a histone lysine methyltransferase. The chemical formula for BIX-01294 is as follows:

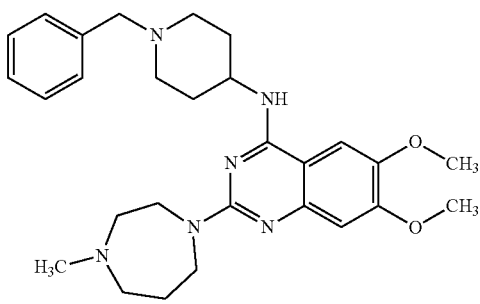 [SMILES: COc1cc2nc(N3CCCN(C)CC3)nc(NC3CCN(Cc4ccccc4)CC3)c2cc1OC]

3-Deazaneplanocin A hydrochloride (DZNep; Tocris Biosciences) is a lysine methyltransferase inhibitor. Specifically, DZNep is an S-Adenosylhomocysteine Hydrolase inhibitor. For example, DZNep inhibits histone methyltransferase EZH2 inhibitor. The chemical formula for 3-Deazaneplanocin A hydrochloride is as follows:

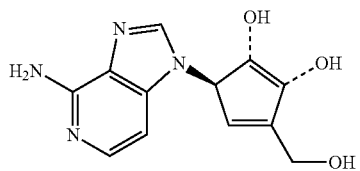

Inhibitors of arginine methyltransferase include AMI-1 ($C_{21}H_{12}N_2Na_4O_9S_2$) (Sigma-Aldrich).

Inhibitors of DNA methyltransferases include 5-aza-cytidine (CAS 320-67-2; Sigma-Aldrich) and 5-aza-2'deoxycytidine (CAS 2353-33-5; Sigma-Aldrich).

Examples of polynucleotides that inhibit histone methyltransferase activity and/or expression include RNA-interfering polynucleotides. For example, siRNAs that specifically bind and target any of the histone methyltransferases disclosed herein, preferably Setdb2, Setd7, Setd8, Prmt7, Ezh1, Ezh2, or Aurkb, for degradation, thereby inhibiting expression or function of the methyltransferase. siRNAs are commercially available and custom designed, synthesized, and purchased, for example, from Dharmacon, Inc. Alternatively, short hairpin RNA (shRNA) sequences can be designed by the skilled artisan using art-recognized techniques and the nucleotide sequences of the methyltransferases disclosed herein.

Examples of polypeptides that inhibit or reduce expression or activity of histone methyltransferases include dominant negative forms of the histone methyltransferase. In this approach, dominant negative mutations (i.e., deletions, substitutions, or truncations) can be designed using the sequences of the methyltransferases disclosed herein and recombinant DNA and protein expression methods well known in the art.

Methods for detecting histone methyltransferase activity are well known in the art. For example, in vitro experiments utilize a substrate (i.e., recombinant histone proteins, or a peptide fragment thereof, preferably containing a methylation site), a histone methyltransferase, and the tested modulator. An assay is then performed to detection of the methylation of the substrate, for example, a colorimetric assay or immunoblotting. Increased or presence of methylation of the substrate indicates that the modulator is an enhancer of histone methylation activity. Decreased or absence of methylation of the substrate indicates that the modulator is an inhibitor of histone methylation activity.

Detection of histone methyltransferase expression can be readily performed by the ordinary artisan. As described herein, RNA is isolated and is reverse-transcribed according to standard protocols. Quantitative RT-PCR expression is performed using target (i.e., histone methyltransferase) primers and/or probes to detect transcripts of the target gene. Protein expression can also be detected using immunoblotting methods known in the art, such as western blotting and ELISA.

Combination Therapy

The compositions disclosed herein can be used in combination with another therapeutic agent for cardiovascular diseases or disorders, or an agent to increase the efficacy of the cardiac reprogramming. The methods disclosed herein further comprise administration of an additional therapeutic agent concurrently, or sequentially.

The combination therapy contemplated by the invention includes, for example, administration of the composition comprising a modulator of a histone methyltransferase as described herein and an additional therapeutic agent in a single pharmaceutical formulation as well as administration with the additional agent(s) in separate pharmaceutical formulations. In other words, co-administration shall mean the administration of at least two agents to a subject so as to provide the beneficial effects of the combination of both agents. For example, the agents may be administered simultaneously, concurrently, sequentially, or in alternative over a period of time.

The agents set forth below are for illustrative purposes and not intended to be limiting. The combinations, which are part of this invention, can be the compounds of the present invention and at least one additional agent selected from the lists below. The combination can also include more than one additional agent, e.g., two or three additional agents if the combination is such that the formed composition can perform its intended function.

The compositions provided herein include more than one histone methylation modulator. For example, the composition includes 2, 3, 4, or 5 histone methylation modulators. In some aspects, the composition includes at least one histone methylation inhibitor or at least one histone methylation enhancer. In other aspects, the composition includes at least one histone methylation inhibitor and at least one histone methylation enhancer.

The compositions provided herein are administered in combination with a second agent, such as a JAK inhibitor or a histone deacetylase inhibitor. The JAK inhibitor or histone deacetylase inhibitor may be administered in a separate or the same pharmaceutical composition as the modulator of histone methylation. When in separate pharmaceutical compositions, the compositions may be administering simultaneously, sequentially, or in alternating pattern.

Suitable JAK inhibitors that can be used in or with the compositions disclosed herein are pan-JAK inhibitors that inhibit JAK-1, JAK-2, and JAK-3 kinases, or any combination thereof. For example, the JAK inhibitor is JAK inhibitor I. In other embodiments, the JAK inhibitor may be an inhibitor that specifically or selectively inhibits at least one of the JAK kinases (JAK1, JAK2, or JAK3). Small molecule inhibitors of JAK-1 such as (INCB018424 (Ruxolitinib) and INCB028050; Incyte Corp.) have been shown to be effective in rheumatoid arthritis models when administered orally. For example INCB028050 is used at a dosage of 10 µg/kg in rodents. Both these inhibitors as well as JAK Inhibitor I (2-(1,1-Dimethylethyl)-9-fluoro-3,6-dihydro-7H-benz[h]- imidaz[4,5-f]isoquinolin-7-one, Pyridone 6, P6, DBI (catalog #420099 from EMD biosciences) have $IC_{50}$ values in the nanomolar range. In the case of #420099, the $IC_{50}$ values against JAK1 and JAK2 are reported to be 15 nM and 1 nM respectively. In the case of INCB018424, the reported $IC_{50}$ values for JAK1 and JAK2 are 3 and 5 nM respectively. INCB018424 and INCB028050 are currently being utilized in clinical trials (Fridman J. S. et al., (2010) Selective Inhibition of JAK1 and JAK2 Is Efficacious in Rodent Models of Arthritis: Preclinical Characterization of INCB028050. J Immunol. 184 (9) 5298-5307).

Other additional therapeutic agents useful for treatment in cardiovascular disease include, but are not limited to, cardiac glycosides, anti-arrhythmic agents, anti-hypertensive agents, anti-hypotensive agents, alpha-adrenergic blockers, beta-adrenergic blockers, calcium channel blockers, cardenolides, ACE inhibitors, diuretics, anti-inflammatory agents (i.e., NSAIDS), angiogenesis agents, anti-angiogenesis agents, vasoconstrictors, vasodilators, inotropic agents, anti-fibrotic agents, and hypolipidemic agents.

Additional agents useful to increase the efficacy or efficiency of reprogramming include, but are not limited to BMP4 (bone morphogenetic protein), valproic acid (histone deacetylase inhibitor), RG108 (DNA methyltransferase inhibitor), R(+) Bay K 8644 (Calcium channel blocker), PS48 (5-(4-Chloro-phenyl)-3-phenyl-pent-2-enoic acid; $Ci_7Hi_5C10_2$) (PDK1 activator), and A83-01 (3-(6-Methyl-2-pyridinyl)-N-phenyl-4-(4-quinolinyl)-1H-pyrazole-1-carbothioamide; C25H19N5S)) (TGFP kinase/activin receptor like kinase (ALK5) inhibitor).

Pharmaceutical Compositions

One or more modulators of histone methyltransferase (HMT) expression or activity can be administered alone to a subject or in pharmaceutical compositions where they are mixed with suitable carriers or excipient(s) at doses for cardiac repair and/or regeneration as described herein. Mixtures of HMT modulators can also be administered to the subject as a simple mixture or in suitable formulated pharmaceutical compositions. For example, one aspect of the invention relates to pharmaceutical composition comprising a therapeutically effective dose of an HMT modulator, or a pharmaceutically acceptable salt, hydrate, enantiomer or stereoisomer thereof; and a pharmaceutically acceptable diluent or carrier.

Techniques for formulation and administration of EZH2 antagonists may be found in references well known to one of ordinary skill in the art, such as Remington's "The Science and Practice of Pharmacy," 21st ed., Lippincott Williams & Wilkins 2005. Suitable routes of administration may, for example, include oral, rectal, or intestinal administration; parenteral delivery, including intravenous, intramuscular, intraperitoneal, subcutaneous, or intramedullary injections, as well as intrathecal, direct intraventricular, or intraocular injections; topical delivery, including eyedrop and transdermal; and intranasal and other transmucosal delivery. Preferably, the HMT modulator is administered in a local rather than systemic matter, for example, via direct intravenous injection, or direct injection to the cardiac tissue. Furthermore, one may administer an EZ1712 antagonist in a targeted drug delivery system.

The pharmaceutical compositions of the present invention may be manufactured, e.g., by conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active HMT modulators into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active HMT modulators in water-soluble form. Additionally, suspensions of the active HMT modulators may be prepared as appropriate oily injection suspensions. Suitable lipophilic solvents or vehicles include fatty oils such as sesame oil, or synthetic fatty acid esters, such as ethyl oleate or triglycerides, or liposomes, Aqueous injection suspensions may contain substances which increase the viscosity of the suspension; such as sodium carboxymethyl cellulose, sorbitol, or dextran. Optionally, the suspension may also contain suitable stabilizers or agents which increase the solubility of the HMT modulators to allow for the preparation of highly concentrated solutions. Alternatively, the active ingredient may be in powder form for reconstitution before use with a suitable vehicle, e.g., sterile pyrogen-free water.

Other delivery systems for hydrophobic pharmaceutical HMT modulators may be employed. Liposomes and emulsions are examples of delivery vehicles or carriers for hydrophobic drugs. Certain organic solvents such as dimethylsulfoxide also may be employed. Additionally, the HMT modulators may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the HMT modulators for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Example 1: MicroRNA-Mediated Reprogramming of Cardiac Fibroblasts

Figure 5:
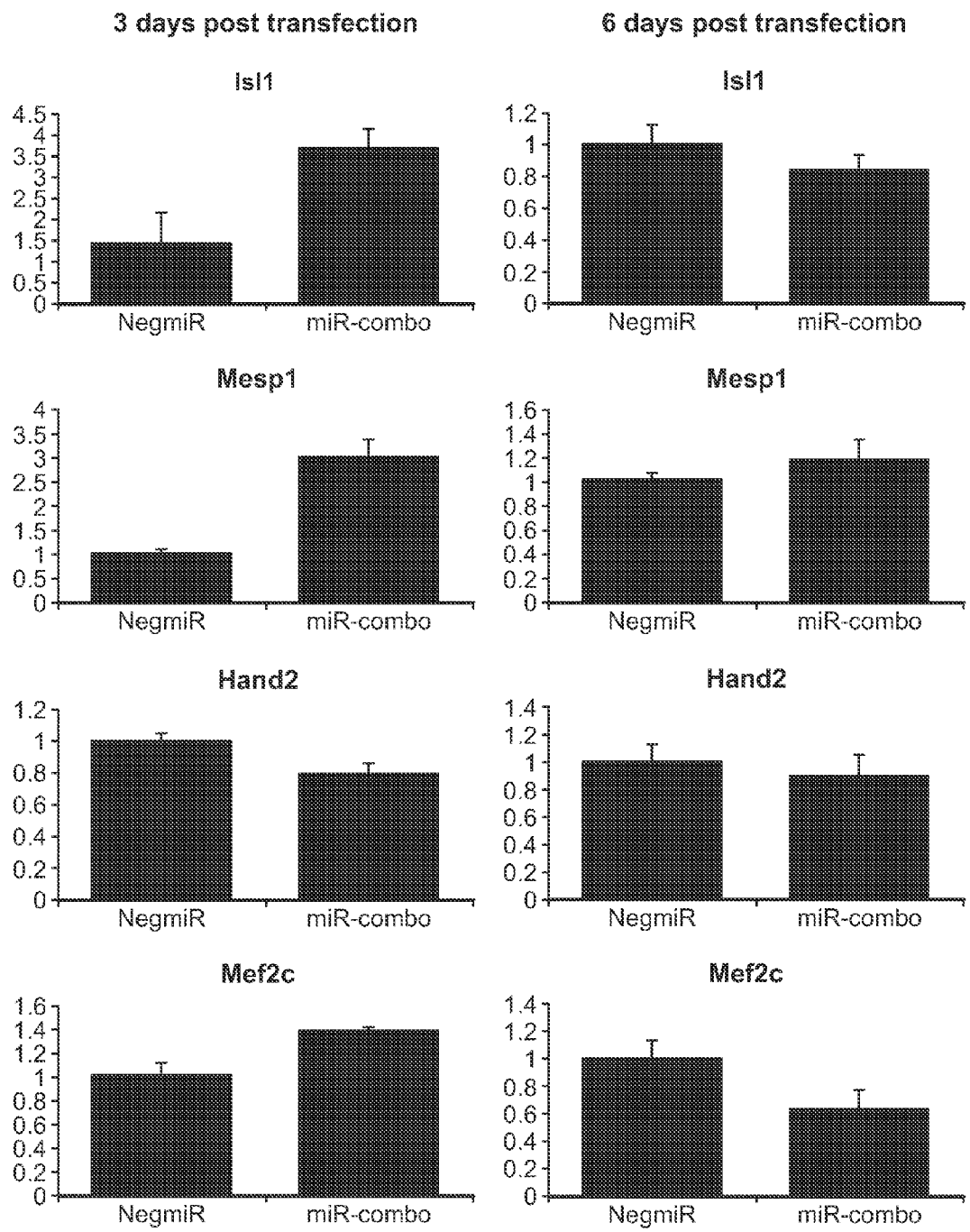
FIG. 5 is a series of bar graphs showing that transfection of human dermal fibroblasts with a combination of miRs induces expression of mesodermal markers as early as 3 d post treatment. Gene expression in fold change normalized to NegmiR transfection for markers of distinct cardiac differentiation stages. All graphs are displayed with SEM.

Mouse cardiac fibroblasts were transfected with specific combinations of distinct microRNAs significant, for example 50 nm each of mir-1, mir-133, mir-208, and mir-499, to cardiac and/or muscle tissue. For all the following methods, the miRNA combination used included miRNAs mir-1, mir-133, mir-208, and mir-499. Quantitative real-time PCR (qRT-PCR) and immunocytochemistry (ICC) were employed to assess a switch in gene expression as early as 3 days following transfection. These techniques make use of specific primers (qRT-PCR) and antibodies (ICC) to detect the expression/upregulation of cardiac differentiation markers. Such markers include MADS box transcription enhancer factor 2, polypeptide C (MEF2C), NK2 transcription factor related, locus 5 (NKX2.5), GATA binding protein 4 (GATA4), heart and neural crest derivatives expressed 2 (HAND2), ISL1 transcription factor, LIM homeodomain (ISL1), troponin I type 3 (cardiac) (TNNI3). FIG. 5 shows that transfection of human dermal fibroblasts with a combination of miRs induces expression of mesodermal markers as early as 3 d post treatment. Gene expression in fold change normalized to NegmiR transfection for markers of distinct cardiac differentiation stages. All graphs are displayed with SEM.

Example 2: Chromatin Modification in Cardiac Reprogramming

Figure 2B:
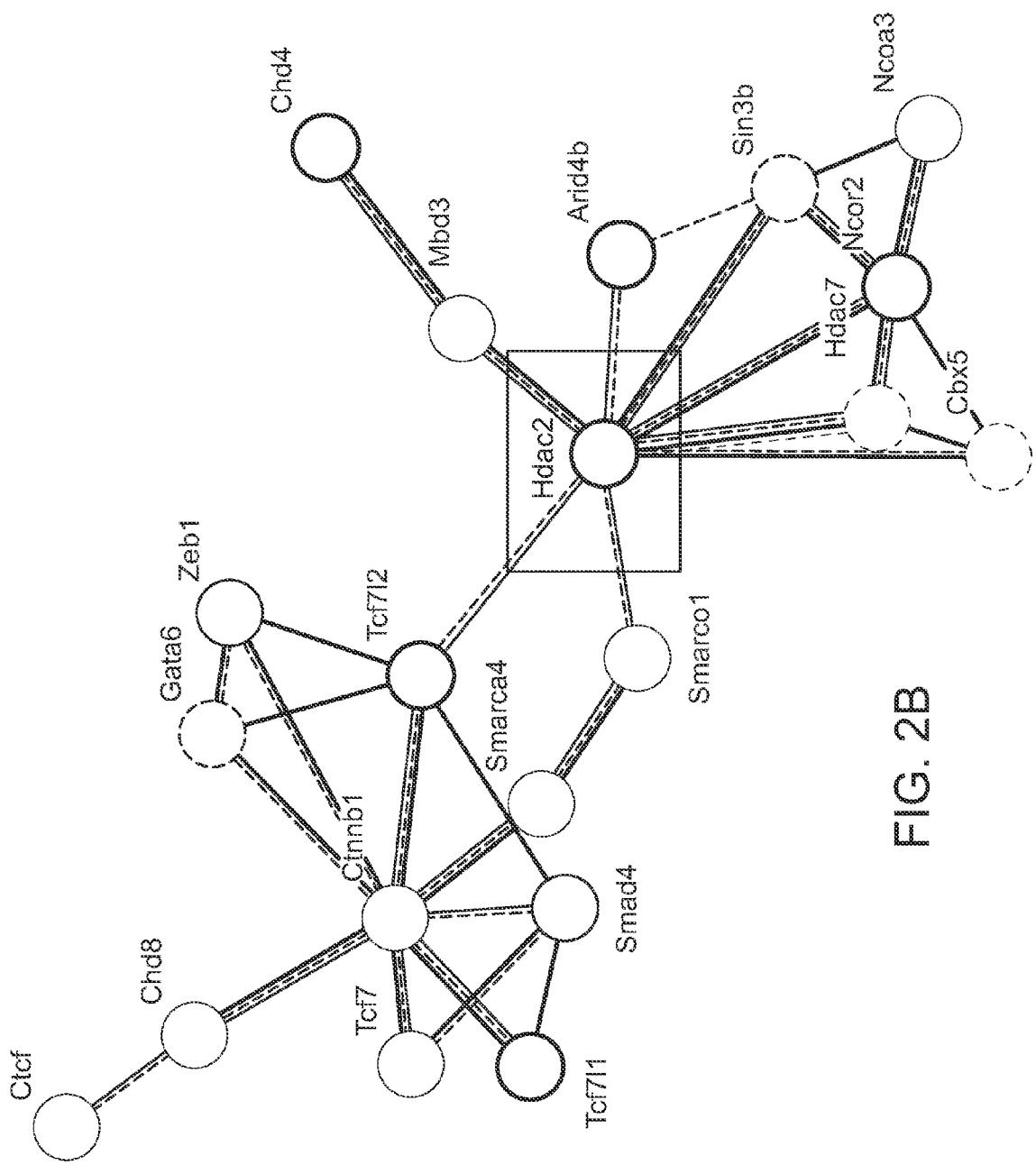
FIG. 2B is a diagram showing that gene enrichment, gene affiliation, and binding information indicated a central role for HDACs in miR mediated reprogramming turning fibroblasts into cardiomyocytes.
Figure 3A:
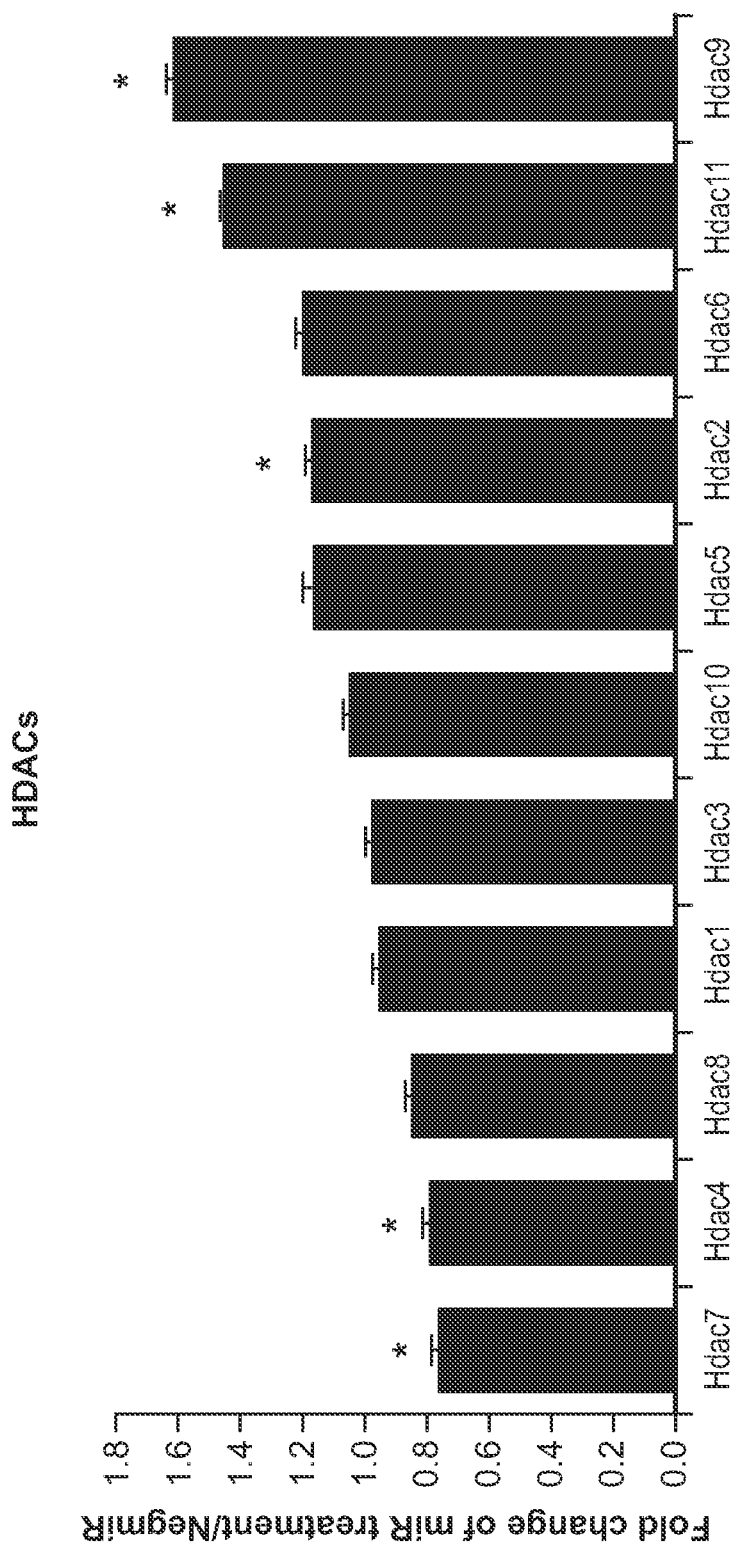

Comparison of gene expression on fibroblasts converted to cardiomyocytes was performed to identify classes or types of genes that were critical for cardiac reprogramming. Microarray analysis was performed using standard tools known in the art. FIG. 2A shows the results of the global gene expression analysis in miR reprogrammed cardiac fibroblasts. Gene affiliation analysis led to the identification of 22 significant terms for molecular function of genes found changed in microarray 9 days post miR transfection. These results showed that 62 of these genes affect chromatin binding. FIG. 2B shows a graphic representation clustering the gene enrichment, gene affiliation and binding information from the microarray analysis, which indicated that histone deacetylases (HDACs, such as HDAC2) play a central role in miR-mediated reprogramming for converting fibroblasts into cardiomyocytes.

Subsequent analysis of histone deacetylase gene expression in fibroblasts and reprogrammed cardiomyocytes showed that some HDAC expression significantly changed after reprogramming, as detected by qPCR and determined by fold change normalized to control NegmiR transfection. For example, Hdac7 and Hdac4 expression was reduced. In contrast, Hdac2, Hdac11, and Hdac9 gene expression was found to be significantly increased.

To confirm these results, fibroblasts transfected with cardiac reprogramming miRNAs or control non-targeting miRNAs (NegmiR) were also treated with different HDAC inhibitors. Several different inhibitors against modifiers of histone acetylation (CPTH2 inhibitors all HAT activity, MC1568 affects HDAC class II, NaB mainly affects HDAC class I, OSU44 inhibits class I, II and IV, Tenovin-1 inhibits all class III Hdacs and XIX Compd2 selectively inhibits HDAC8). All inhibitors were administered 24 hours post treatment. Gene expression of cardiac transcription factors was measured 6 d post transfection. Cardiac markers, such as Hand2, Gata4 and Tbx5 were determined by qPCR. Some HDACs were shown to have some role in enhancing or inhibiting cardiac reprogramming.

Example 3: Histone Methyltransferases in Cardiac Reprogramming

Figure 4A:
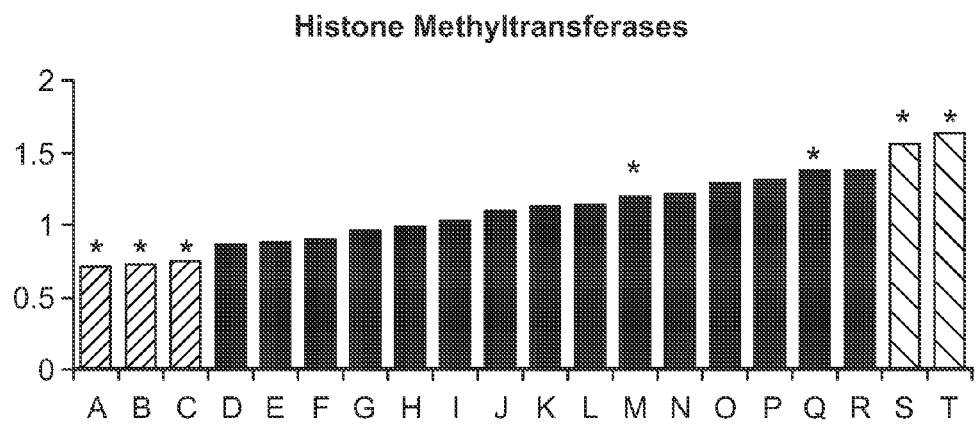
FIG. 4A is a bar graph showing that histone methyltransferases have an altered gene expression profile in miR treated cardiac fibroblasts. Fold changes normalized to NegmiR transfected cells are presented. Data are shown as mean±SEM. *P<0.05. A=X; B=Prmt6; C=Dnmt3b, D=Dnmt1, E=Suv39h1; F=Mll5; G=Ehmt1; H=Smyd3; I=Prmt2; J=Prmt1; K=Prmt5; L=Mll3; M=Ehmt2; N=Carm1; O=Prmt3; P=Prmt8; Q=Dot11; R=Smyd1; S=Y; T=Z.

Fibroblasts transfected with cardiac reprogramming miRNAs or control non-targeting miRNAs (NegmiR) were also treated with different HDAC inhibitors. Gene expression of many histone methyltransferases were determined using qPCR, for example, Prmt6, Dnmt3b, Dnmt1, Suv39h1, Mll5, Ehmt1, Smyd3, Prmt2, Prmt1, Prmt5, Mll3, Ehmt2, Carm1, Prmt3, Prmt8, Dot1L, and Smyd1. FIG. 4A shows that histone methyltransferases have an altered gene expression profile in miR treated cardiac fibroblasts.

Figure 4B:
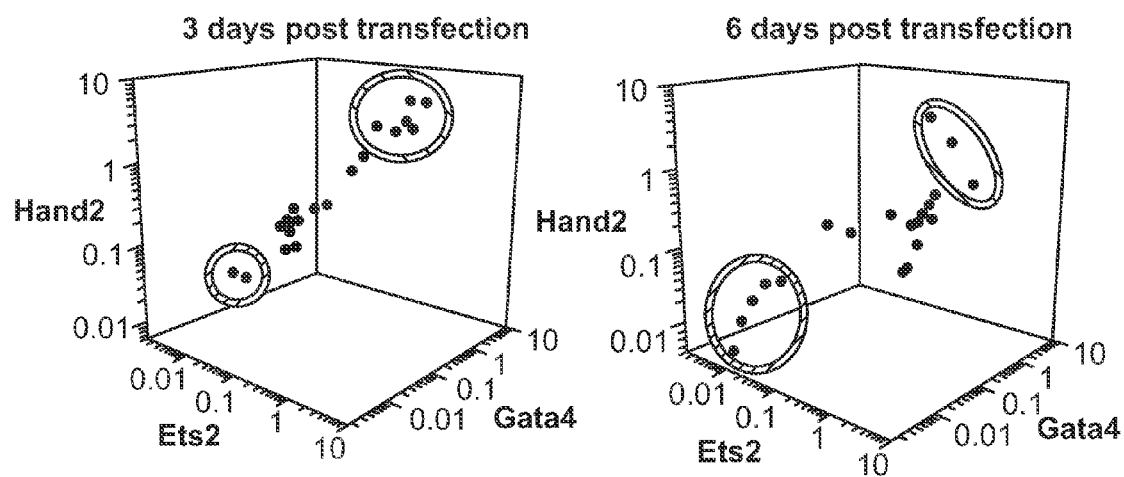
FIG. 4B is a three-dimensional dot plot showing cardiac transcription factor gene expression. RNAi screening for candidate genes. These results indicate that histone methyltransferase inhibition plays a role in miR mediated cardiac reprogramming. The circled datapoints indicate histone methyltransferase genes.

Comparison of all the gene expression data for cardiac markers Hand2, Ets2, and Gata4 at 3 days after transfection (FIG. 4B, left) and 6 days after transfection (FIG. 4B right) showed that histone methyltransferase inhibition plays a role in miR mediated cardiac reprogramming. The circled datapoints represent histone methyltransferases and demonstrate that their expression and activity plays a critical role in cardiac reprogramming.

Figure 6A:
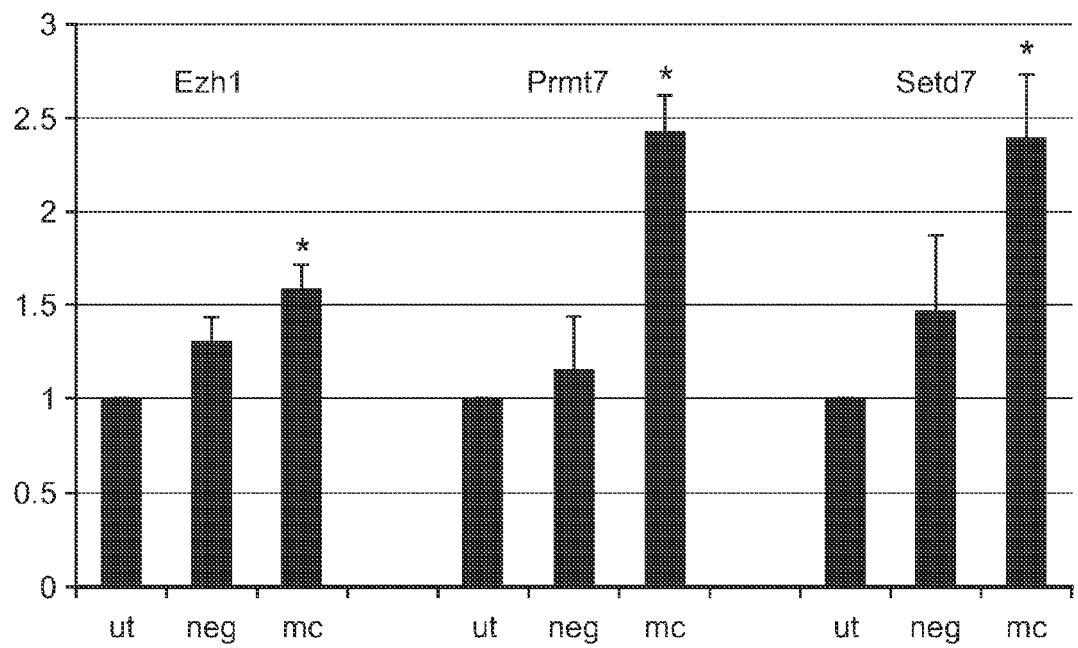
FIG. 6 is two bar graphs showing that epigenetic modifiers expression is changed upon microRNA-mediated cardiac reprogramming. Neonatal mouse cardiac fibroblasts were transfected with the microRNA combination and RNA was isolated 3-4 days afterwards for gene expression analysis by qRT-PCR. (A) Gene expression was analyzed for epigenetic modifiers Ezh1, Prmt7, Setd7. (B) Gene expression was analyzed for epigenetic modifiers Ezh2, Setd8, and Aurkb. The data are shown as Average+/−Standard deviation. Ut: Untreated; Neg: negative control scrambled microRNA, mc: microRNA combination (50 nM of a combination of miR-1, miR-133, miR-208, miR-499).
Figure 6B:
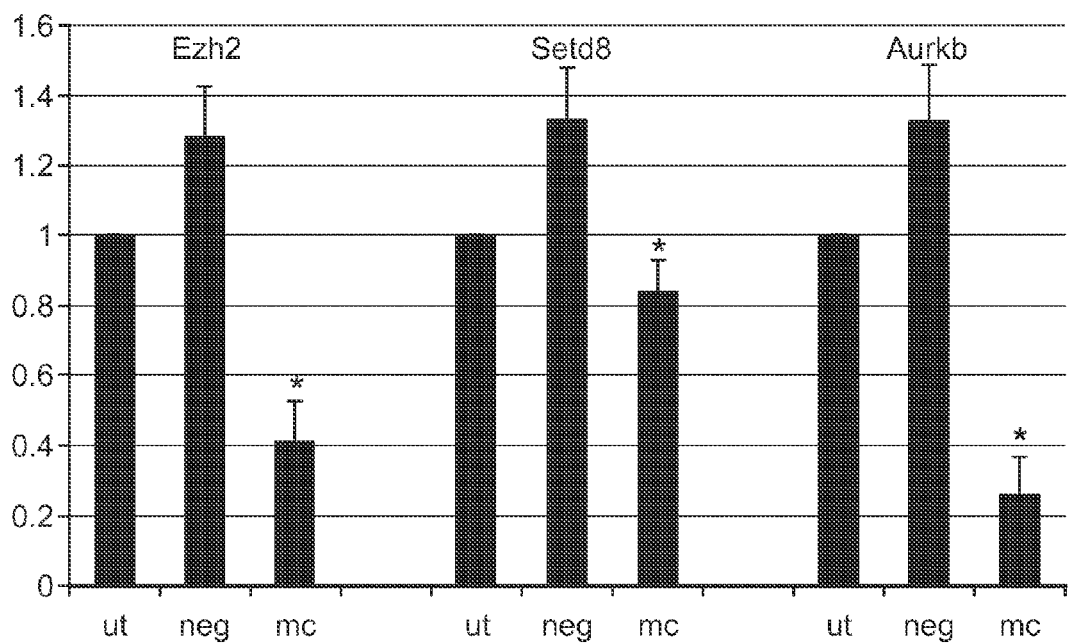
Figure 7:
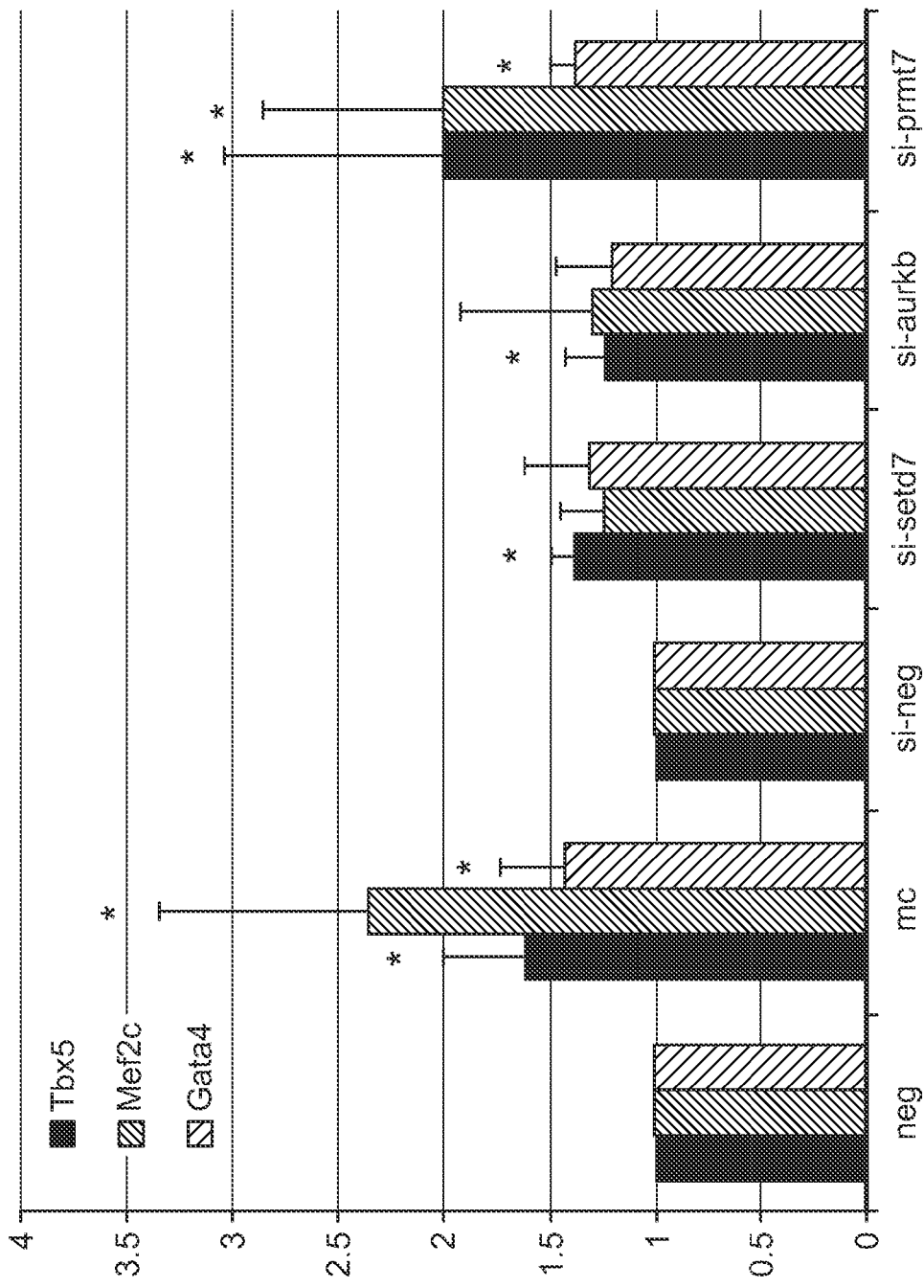
FIG. 7 is a graph showing how epigenetic modifiers affect cardiac reprogramming. Neonatal mouse cardiac fibroblasts were transfected with the microRNA combination (50 nM) or with siRNAs against the indicated genes (40 nM), Setd7, Aurkb, and Prmt7. Gene expression analysis of cardiac markers Tbx5, Mef2c, and Gata-4 were determined by qRT-PCR. The data are shown as Avg+/Sdv. Neg: negative control scrambled microRNA, mc: microRNA combination, si-neg: negative control scrambled siRNA. Neg and mc serve as reference controls for reprogramming. *P<0.05 vs si-neg.

Additional experiments were performed in neonatal mouse cardiac fibroblasts were transfected with the microRNA combination. RNA was isolated 3-4 days afterwards for gene expression analysis by qRT-PCR. In FIG. 6A, histone methyltransferases Ezh1, Prmt7, and Setd7 were shown to be significantly increased after miR-mediated cardiac reprogramming. In contrast, histone methyltransferases Ezh2, Setd8, and protein Aurkb gene expression was shown to be significantly decreased after miR-mediated cardiac reprogramming when compared to both untreated and control negative control scrambled microRNA-treated cells. These results demonstrated that inhibition or enhancement of histone methyltransferase activity or expression plays a significant role in cardiac reprogramming of fibroblast cells.

Example 4: Models of Cardiac Reprogramming

Animal models of cardiovascular diseases are well known in the art. For example, myocardial infarction mouse models have been developed, in which coronary artery ligation is performed to induce myocardial infarction. Transgenic models of hypertension have also been developed, for example, the TGR(mREN)27 transgenic rat. Also, hypertension can be induced in animal models using infusion of angiotensin II (AngII) or chronic oral administration of NO synthase inhibitor. Cardiac fibrosis or presence of fibrotic tissue are determined using methods known in the art, for example by biopsy, or histopathological analysis of the heart (i.e., staining sections of the heart with fibroblast markers, collagen I, II or IV, or using trichrome or picro Sirius red staining).

Animals that suffer from fibrotic tissue are administered a composition comprising a modulator of a histone methyltransferase, BIX-01294 or DZNep, or a control composition. Animals are monitored for morbidity, lethargy, appetite, and sleep cycles. Cardiac tissue is harvested at various timepoints for cardiac marker or fibroblast gene expression analysis by qPCR or immunohistochemistry to identify increase in the expression of cardiac markers, particularly at the site of the fibrotic tissue. Other factors regarding improved cardiac function are assessed, such as blood pressure, exercise capacity, and collagen deposition in cardiac muscle. Animals are also monitored over extended time for observation of reoccurrence of cardiovascular disease.

Cell replacement therapy is also tested in the animal models suffering from cardiac fibrosis. Fibrosis, cardiovascular disease, or injury to the heart is performed using methods known in the art or the mouse models described above. Fibroblasts isolated from the animal subject, such as the skin fibroblasts, or cardiac fibroblasts isolated from a biopsy, are treated with a composition comprising a modulator of histone methyltransferase and are subsequently cultured and expanded under the appropriate conditions to promote cardiac reprogramming Subsequent testing of the cultured reprogrammed cells for expression of cardiac cell markers or cardiac cell function (for example, pulsing or beating movement) is used to verify successful reprogramming Cells are then collected, purified, and then transplanted into the subject animal Animals are subsequently monitored for improvement in cardiac function and/or reduction in fibrotic tissue in the heart.

These models demonstrate that composition comprising modulators of histone methylation compounds convert fibrotic tissue or fibroblasts to repair or regenerate functional cardiac tissue.

Example 5: Inhibition of Histone Methyltransferase Expression or Activity in Cardiac Reprogramming Neonatal mouse cardiac fibroblasts were transfected with the microRNA combination (50 nM) or with siRNAs against the indicated genes (40 nM), Setd7, Aurkb, and Prmt7. Efficient knockdown (or reduction in protein expression) was verified by western blotting. Gene expression analysis of cardiac markers Tbx5, Mef2c, and Gata-4 were determined by qRT-PCR. Fold changes in the expression data were normalized to control NegmiR treated cells. Fibroblasts treated with the combination of cardiac reprogramming miRs (mir-1, mir-133, mir-208, and mir-499) were used a positive control to show successful cardiac reprogramming SiRNAs against specific histone methyltransferases showed successful reprogramming for at least one cardiac marker. Inhibition of expression or activity of Prmt7 showed significant upregulation of all cardiac markers tested.

Figure 9A:
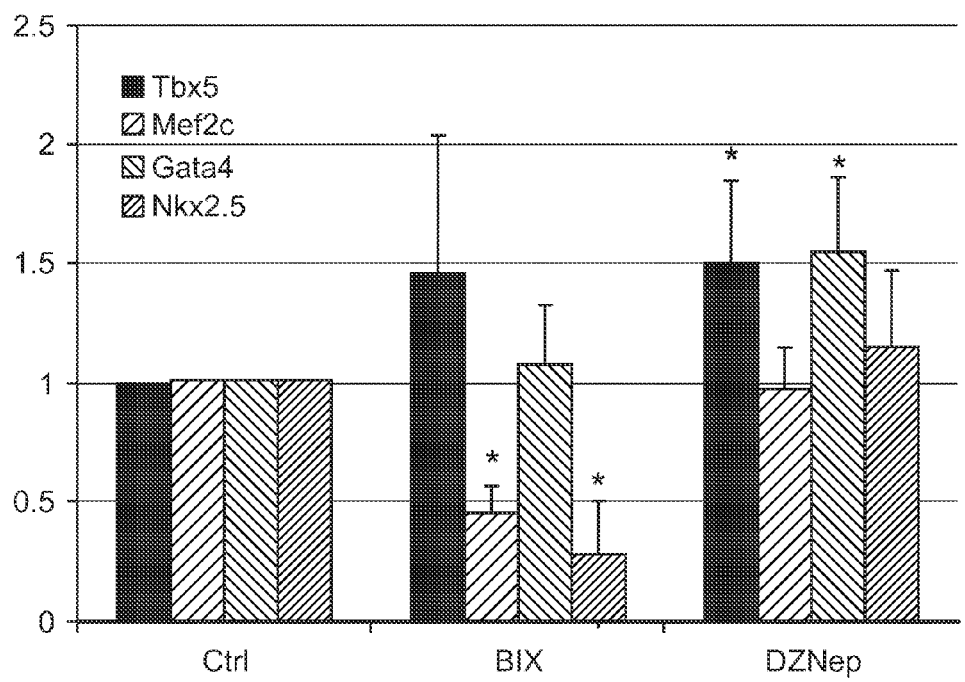
FIG. 9 is two bar graphs demonstrating that inhibition of histone methyltransferases affect cardiac markers expression. Neonatal cardiac fibroblasts were treated with 1 µM of the H3K9me3 inhibitor BIX-01294 (BIX) or 1 µM of the H3K27me3/H4K20me3 inhibitor 3-Deazaneplanocin A hydrochloride (DZNep) from day 1 to day 3 in the absence (A) or presence of microRNA combination (MC) (B). Gene expression of cardiac markers was assessed by qPCR. Data are shown as Avg+Sdv. *P<0.05.

Inhibition of histone methyltransferase activity by small molecule compounds was investigated. Neonatal cardiac fibroblasts were treated with 1 µM of the H3K9 methylation inhibitor BIX-01294 or 1 µM of the H3K27/H4K20 methylation inhibitor 3-Deazaneplanocin A hydrochloride (DZNep). After 3 days, RNA was harvested using standard protocols known in the art, and cardiac gene expression was assessed by qPCR. The cardiac genes tested were Tbx5, Mef2C, Gata4, and Nkx2.5. As shown in FIG. 9A, treatment with BIX resulted in significant downregulation of Mef2C and Nkx2.5 cardiac markers. In contrast, treatment with DZNep resulted in significant upregulation of cardiac markers Tbx5 and Gata4. These results show that enhancement of H3K9 methylation is useful for expression of some cardiac markers. Alternatively, inhibition of H3K9 causes upregulation of other cardiac markers, such asTbx5, and therefore inhibition of H3K9 methylation also promotes the expression of at least one cardiac marker. These results indicate that inhibition of H3K27 methylation, and the methyltransferases that produce methylated H3K27, leads to reprogramming of fibroblasts into cardiomyocytes as evidenced by the induction of expression of cardiac marker in fibroblasts.

Figure 9B:
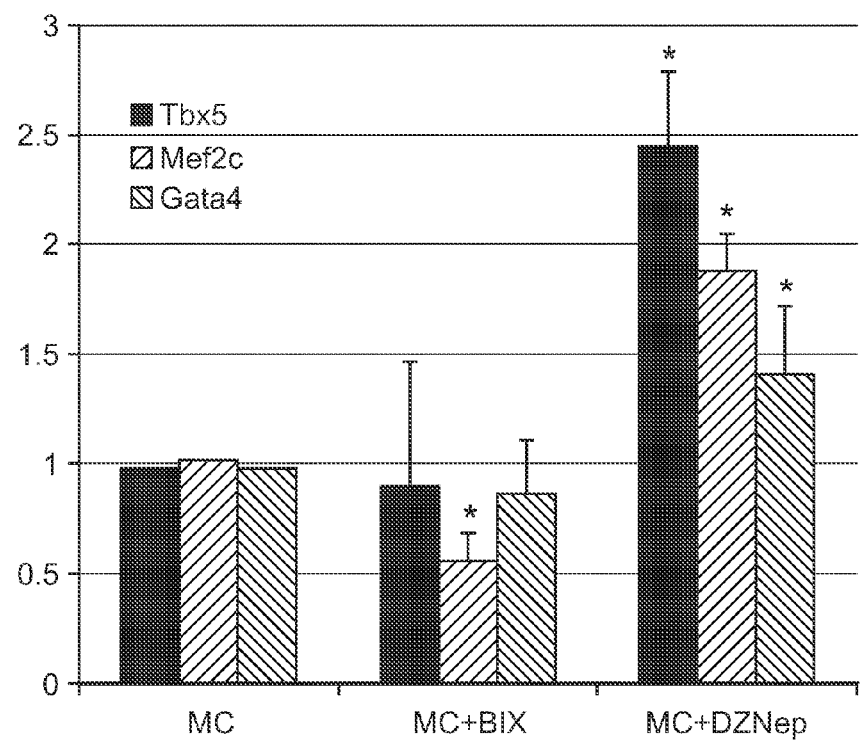
Figure 10A:
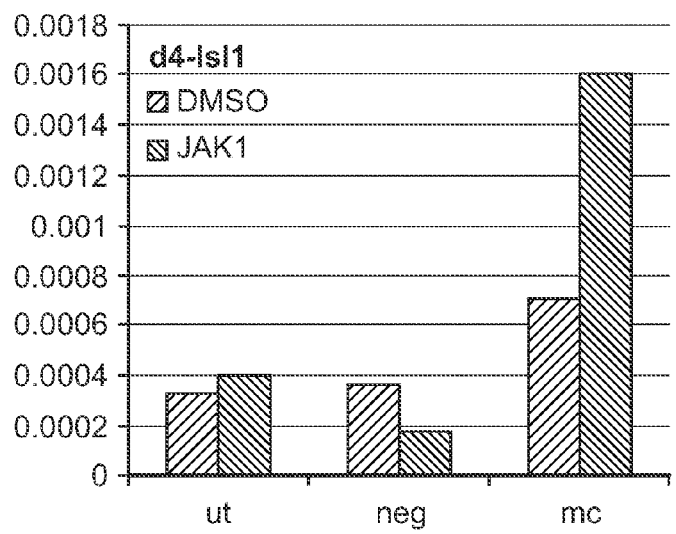
FIG. 10 is a series of six bar graphs showing the enhancement of microRNA mediated cardiac reprogramming as measured by cardiac transcription factor expression in human fibroblasts (BJ cells) by the addition of control (DMSO) or pan-JAK inhibitor I (1 µM) (right bar values). Gene expression was determined by qPCR. (A) Isl-1 gene expression. (B) Mesp2 gene expression. (C) Tbx5 gene expression. (D) Mef2c gene expression. (E) Gata-4 gene expression. (F) Hand2 gene expression. unt: Untreated; neg: Negative microRNA control (50 µM), mc: cells treated with the microRNA combination (50 µM).
Figure 10B:
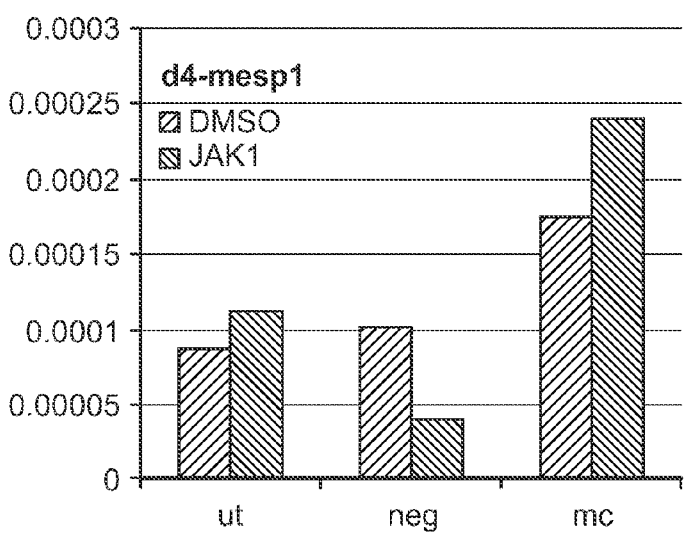
Figure 10C:
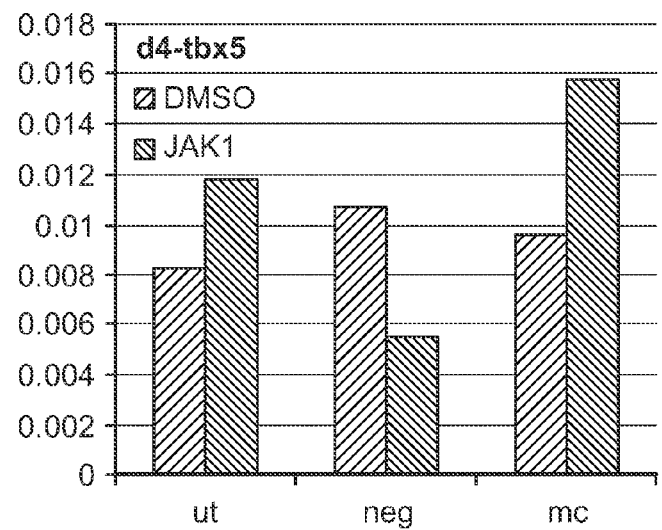
Figure 10D:
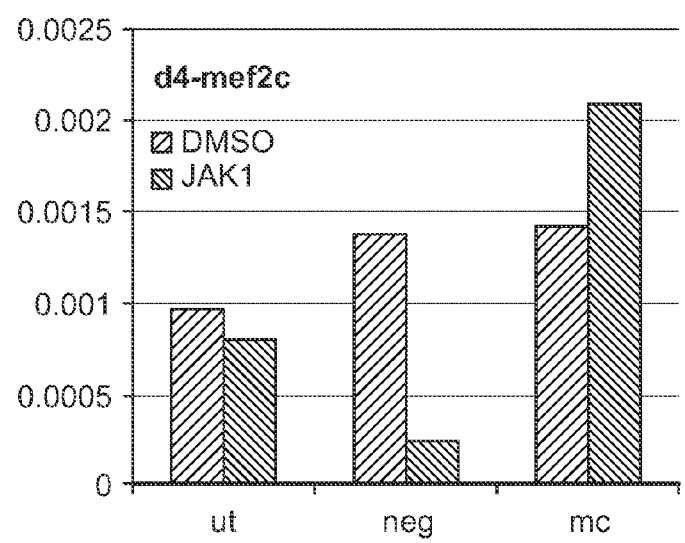
Figure 10E:
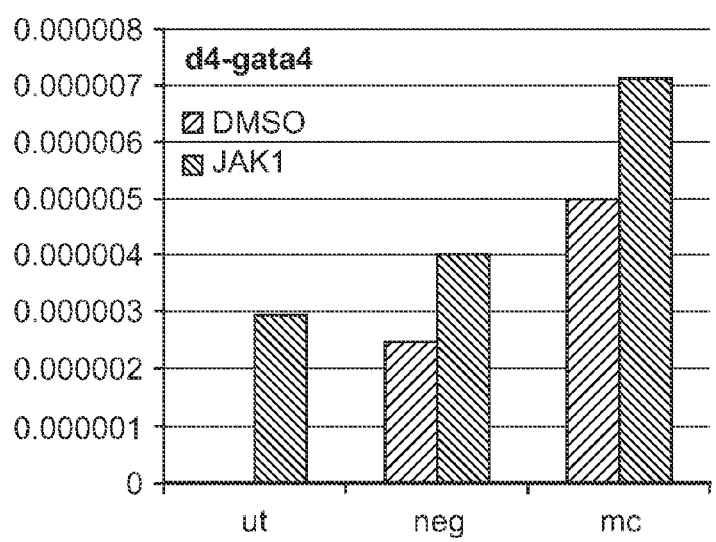
Figure 10F:
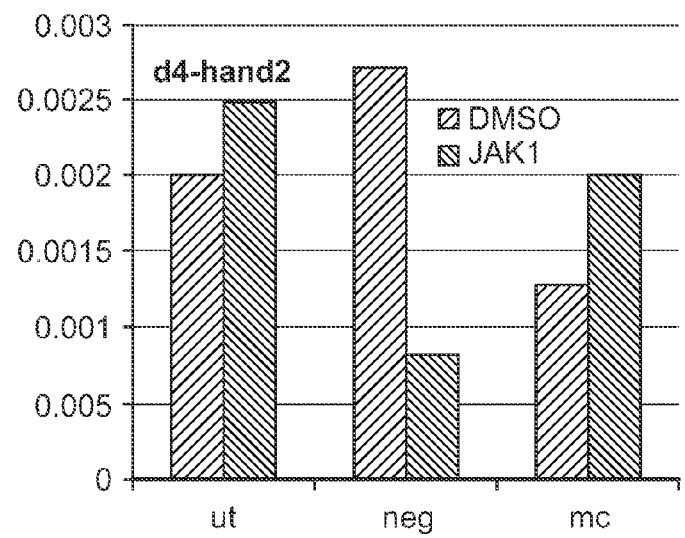

Neonatal cardiac fibroblasts that were transfected with miRNAs that induce cardiac reprogramming were also treated with 1 µM of the H3K9 methylation inhibitor BIX-01294 or 1 µM of the H3K27/H4K20 methylation inhibitor 3-Deazaneplanocin A hydrochloride (DZNep). Analysis was performed similarly as described above, and the cardiac gene expression was assessed by qPCR. As shown in FIG. 9B, miR-mediated reprogrammed cells that were also treated with DZNep had significantly increased expression of all three tested cardiac markers, Tbx5, Mef2c, and Gata4. Thus, inhibition of H3K27 methylation and the methyltransferases that confer methylated H3K27 synergizes with the reprogramming capacity of the miRNAs.

Genetic tools and cell sorting methods were utilized to determine the efficiencies of converting cardiac fibroblasts to cardiac myocytes using the methods described herein. Specifically, neonatal mouse cardiac fibroblasts were isolated from a transgenic model where the cyan fluorescent protein (CFP) reporter is driven by the myosin heavy chain alpha (alphaMHC) reporter, which is specifically "turned on" in cardiac myocytes. Thus, the starting cell population of cardiac fibroblasts is CFP negative. These cells were then transfected with the miRNA combination that induces cardiac reprogramming.

Figure 8A:
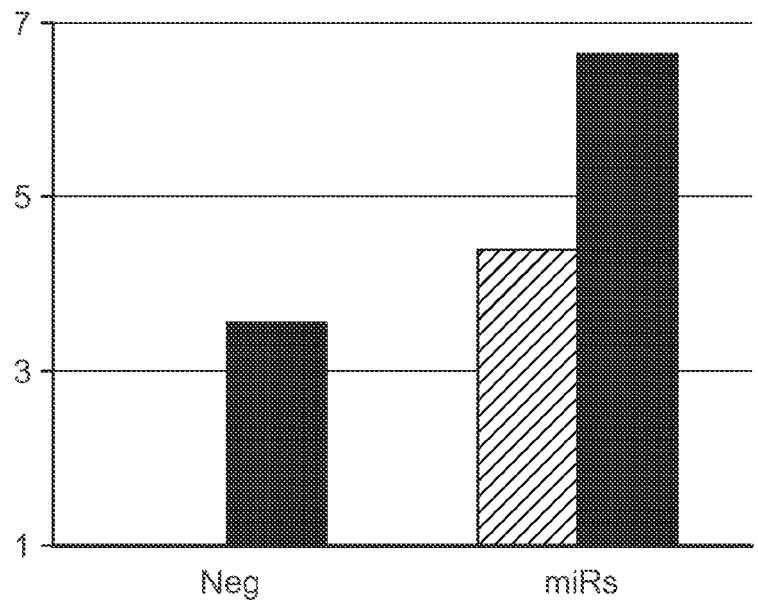
FIG. 8 is two bar graphs showing cardiomyocyte expression of alpha-myosin heavy chain (MHC)-CFP reporter. Neonatal cardiac fibroblasts transgenic for the reporter construct: alpha-myosin heavy chain (MHC) promoter linked to cyan fluorescent protein (CFP) under the control of the alpha-MHC promoter. (A) Cells were transfected with miR-NAs (50 nM), siRNA (40 nM) against Setdb2 or both. Neg-siRNA was used as a control for Setdb2 siRNA. The cells were isolated 6 days after treatment and subjected to FACS analysis for alpha-MHC driven CFP expression. (B) Neg-siRNA control or miRNA-transfected cells were treated with BIX-01294 (used at a final concentration of 1 µM) from day 2 to day 6.
Figure 8B:
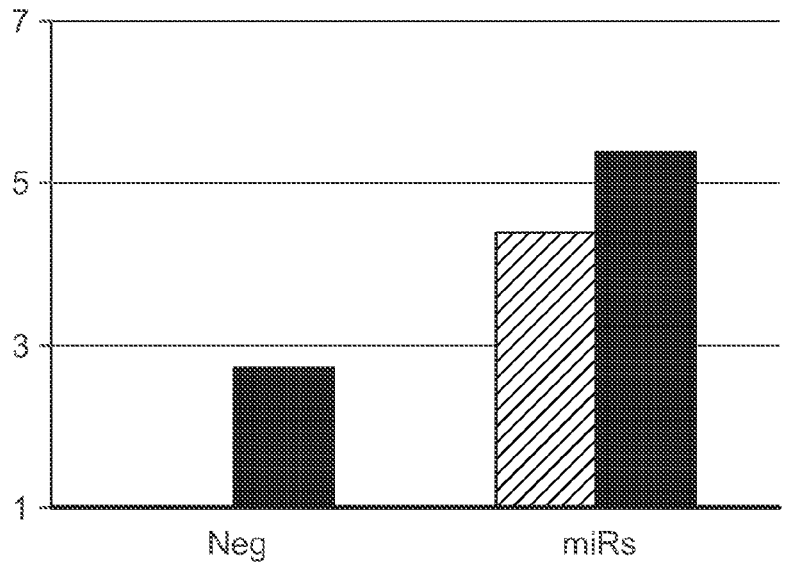

Cells were also transfected either with siRNA targeting histone methyltransferase Setdb1, or treated with histone methyltransferase inhibitor BIX-01294. CFP positive cell population was sorted, and the percentage of CFP positive cells is shown in FIGS. 8A and 8B. In both experiments, miRNA-mediated reprogramming consistently increased CFP-positive cells by 3-5% percent of the overall population Inhibition of histone methylation without miRNA-mediated reprogramming also results in increased cardiomyocyte CFP-positive cells, between 2.5-3.5%. The results further indicate that inhibition of histone methyltransferases in addition to miRNA-mediated reprogramming increased cardiomyocyte conversion even further, such that 5-7% of the population were converted to cardiomyocytes.

This method is also used to test the increase in efficacy or efficiency of reprogramming for combination therapies, i.e., with two or more histone methylation modulators, or at least one histone methylation modulator in combination with a second therapeutic agent.

Example 6: JAK Inhibition Enhances Cardiac Reprogramming

Human fibroblasts (BJ clls) were transfected with the combination of miRNAs that induce cardiac reprogramming. Transfected cells were treated with either DMSO or JAK inhibitor I (a pan-JAK kinase inhibitor). RNA was harvested and prepared according to standard protocols for qPCR gene expression analysis. The expression of cardiac marker genes, such as Isl1, Mesp1, Tbx5, Mef2c, Gata4, and Hand2 was assessed. The results as shown in FIGS. 10A-10F demonstrate that treatment with JAK inhibitors, such as JAK inhibitor I, causes increases in expression of cardiac markers when compared to cells that were transfected with the miRNAs alone. Thus, JAK inhibition enhances the cardiac reprogramming.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for promoting the reprogramming of a non-cardiomyocytic cell or tissue into cardiomyocytic cell or tissue comprising contacting said non-cardiomyocytic cell or tissue with a composition comprising an inhibitor of histone methyltransferase activity or expression, and one or more of mir-1, mir-133, mir-208, and mir-499, wherein said non-cardiomyocytic cell is directly reprogrammed into cardiomyocytic tissue without a stem cell intermediary state.

2. The method of claim 1, wherein said inhibitor comprises a small molecule, a polynucleotide, or a polypeptide.

3. The method of claim 1, wherein said inhibitor inhibits or reduces the expression or activity of Setdb2, Prmt7, Setd7, Setd8, Ezh1, Ezh2, or Aurkb.

4. The method of claim 1, wherein said inhibitor inhibits or reduces methylation of lysine at position 9 on histone H3 (H3K9), lysine at position 27 on histone H3 (H3K27), or arginine at position 3 on histone H4 (H4R3).

5. The method of claim 1, wherein the inhibitor of histone methyltransferase activity is 2-(Hexahydro-4-methyl-1H-1,4-diazepin-1-yl)-6,7-dimethoxy-N-[1-(phenylmethyl)-4-piperidinyl]-4-quinazolinamine trihydrochloride hydrate (BIX-01294) or 3-Deazaneplanocin A hydrochloride (DZNep).

6. The method of claim 1, wherein said modulator comprises an enhancer of histone methyltransferase activity.

7. The method of claim 1, wherein said modulator enhances or increases methylation of lysine at position 9 on histone H3 (H3K9), lysine at position 27 on histone H3 (H3K27), or arginine at position 3 on histone H4 (H4R3).

8. The method of claim 1, wherein said modulator enhances or increases the expression or activity of Setdb2, Prmt7, Setd7, Setd8, Ezh1, Ezh2, or Aurkb.

9. The method of claim 1, further comprising the administration of a JAK inhibitor or a histone deacetylase inhibitor.

10. The method of claim 9, wherein said JAK inhibitor inhibits or reduces the activity or expression of JAK-1, JAK-2, or JAK-3.

11. The method of claim 9, wherein the JAK inhibitor is JAK inhibitor-I.

12. The method of claim 1, wherein said non-cardiomyocytic cell or tissue comprises cardiac fibrotic tissue.

13. The method of claim 1, wherein said non-cardiomyocytice cell comprises a fibroblast, adipocyte, or a hematopoietic cell.

14. The method of claim 13, wherein said hematopoietic cell is a $CD34^+$ umbilical cord blood cell.

15. The method of claim 1, wherein said cardiomyocytic tissue is characterized by an increased expression of a cardiomyocyte marker protein after said contacting step compared to the level of said marker protein before said contacting step.

16. The method of claim 15, wherein said marker protein is selected from the group consisting of sarcomeric actinin, L-type calcium channel, brachyury, Flk1, Islet1, Mesp1, Gata4, Mef2c, Hand2, TroponinT2, and Tbx-5.

17. The method of claim 12, wherein said fibrotic tissue is present in a heart diagnosed as comprising myocardial infarction, ischemic heart disease, hypertrophic cardiomyopathy, valvular heart disease, congenital cardiomyopathy, hypertension, or other cardiac disease or condition associated with fibrosis.

18. The method of claim 1, wherein contacting comprises intravenous administration or direct injection into cardiac tissue.

19. The method of claim 1, wherein said contacting occurs ex vivo.

20. The method of claim 19, further comprising delivering the reprogrammed cardiomyocyte cell or tissue to the heart of a subject in need thereof.

21. The method of claim 20, wherein said delivering comprises intravenous administration or direct injection into cardiac tissue.

* * * * *